(12) United States Patent
Sheppard et al.

(10) Patent No.: US 6,787,322 B2
(45) Date of Patent: Sep. 7, 2004

(54) METHODS OF EXPRESSING INTEGRIN $\beta_6$ SUBUNITS

(75) Inventors: Dean Sheppard, Oakland, CA (US); Robert Pytela, San Francisco, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 10/219,631

(22) Filed: Aug. 14, 2002

(65) Prior Publication Data

US 2003/0064471 A1 Apr. 3, 2003

Related U.S. Application Data

(60) Continuation of application No. 10/072,841, filed on Feb. 6, 2002, which is a continuation of application No. 09/591,543, filed on Jun. 8, 2000, now abandoned, which is a division of application No. 08/938,085, filed on Sep. 26, 1997, now Pat. No. 6,339,148, which is a division of application No. 07/728,215, filed on Jul. 11, 1991, now Pat. No. 5,962,643.

(51) Int. Cl.[7] ............................................. G01N 33/567
(52) U.S. Cl. ...................... 435/7.21; 435/69.1; 435/7.1; 435/7.2; 536/23.1; 536/23.5
(58) Field of Search ................................ 435/69.1, 7.1; 536/23.1, 23.5

(56) References Cited

U.S. PATENT DOCUMENTS

| 5,204,445 A | | 4/1993 | Plow et al. |
| 5,739,032 A | * | 4/1998 | Springer et al. |
| 6,339,148 B1 | * | 1/2002 | Sheppard et al. |

OTHER PUBLICATIONS

Cheresh, et al., "A Novel Vitronectin Receptor Integrin ($\alpha_{vi}\beta_x$) Is Responsible for Distinct Adhesive Properties of Carcinoma Cells"; *Cell* vol. 57, p. 59–69 (Apr. 1989).

Freed, et al., "A novel intergrin $\beta$ subunit is associated with the vitronectin receptor $\alpha$ subunit ($\alpha_v$) in a human osteosarcoma cell line and is a substrate for protein kinase C" *The EMBO Journal* vol. 8, No. 10, p. 2955–2965 (1989).

Holzmann, et al., "Identification of a Murine Peyer's Patch–Specific Lymphocyte Homing Receptor as an Integrin Molecule with an $\alpha$ Chain Homologous to Human VLA–4$\alpha$"; *Cell*, vol. 56, p. 37–46 (Jan. 1989).

Kajiji, et al., "A novel integrin ($\alpha_E\beta_4$) from human epithelial cells suggests a fourth family of integrin adhesion receptors"; *The EMBO Journal* vol. 8, No. 3, p 673–680 (1989).

Kramer, et al. "Integrin Structure and Ligand Specificity in Cell–Matrix Interactions"; *Molecular and Cellular Aspects of Basement Membranes*, edited by David H. Rohrbach and Rupert Timpl, Chapter 12, pp. 239–265 (1993).

Ruoslahti, et al. "New Perspectives in Cell Adhesion: RGD and Integrins"; *Science*, vol. 238, pp. 491–497(Oct. 1987).

Ramaswamy, et al., "Cloning, primary structure and properties of a novel human integrin $\beta$ subunit"; *The EMBO Journal*, vol. 9, No. 5, p. 1561–1568 (1990).

Sheppard, et al., "Complete Amino Acid Sequence of a Novel Integrin $\beta$ Subunit ($\beta_6$) Identified in Epithelial Cells Using the Polymerase Chain Reaction"; *The Journal of Biological Chemistry*, vol. 265, No. 20, p. 11502–11507 (1990).

Sheppard, et al. "Use of Homology PCR to Identify a Novel Integrin Beta Chain from Airway Epithelium"; *Am. Rev. Respir. Dis.*, 141:A707 World Conference on Lung Health, Boston Mass. May 20–24, 1990.

\* cited by examiner

*Primary Examiner*—Phillip Gambel
(74) *Attorney, Agent, or Firm*—Townsend and Townsend and Crew LLP

(57) ABSTRACT

The present invention provides substantially pure integrins containing a novel $\beta$ subunit designated as $\beta_6$. The novel $\beta_6$ subunit forms heterodimers with $\alpha_V$ and $\alpha_F$. Methods of controlling cell adhesion using the $\beta_6$-containing integrins are also provided.

1 Claim, 11 Drawing Sheets

FIGURE 1A

CONSENSUS β SUBUNIT PRIMERS

```
β₂ human   GACCTGTACTATCTGATGGACCT       β₂ human   GAGGGTGGGCTGGACGCCATGATGCA
           D  L  Y  Y  L  M  D  L                   E  G  G  L  D  A  M  M  Q
β₃ human   GACATCTACTACTTGATGGACCT       β₃ human   GAGGGTGGCTTGATGCCATCATGCA
           D  I  Y  Y  L  M  D  L                   E  G  G  F  D  A  I  M  Q
β₁ human   GACCTCTACTACCTTATGGACCT       β₁ human   GAAGGTGGTTTCGATGCCATCATGCA
           D  L  Y  Y  L  M  D  L                   E  G  G  F  D  A  I  M  Q
β₁ chicken GACCTTTATTATCTTATGGACCT       β₁ chicken GAAGGTGGATTGATGCAATAATGCA
           D  L  Y  Y  L  M  D  L                   E  G  G  F  D  A  I  M  Q
```

PRIMER B1F  5' GACCTCTACTACCTGATGGACCT 3'       PRIMER B2E  3' CTTCCACCTAATCTACGGTATTACG 5'
```
                      A G   T  TT T                                 C        G    G    T
```

```
β₂ human   GGGGACTGTGTCTGCGGGCAGTGC      β₂ human   ATCGGCATTCTCCTGCTGGTCATCTGGAAG
           G  D  C  V  C  G  Q  C                   I  G  I  L  L  L  V  I  W  K
β₃ human   GGCGAGTGCCTCTGTGGTCAATGT      B₃ human   ATTGGCCTTGCCGCCCTGCTCATCTGGAAA
           G  E  C  L  C  G  Q  C                   I  G  L  A  A  L  L  I  W  K
β₁ human   GGAGAGTGCGTCTGCGGACAGTGT      B₁ human   ATTGGCCTTGCATTACTGCTGATATGGAAG
           G  E  C  V  C  G  Q  C                   I  G  L  A  L  L  L  I  W  K
β₁ chicken GGAGAGTGCATTTGCGGACAGTGC      β₁ chicken ATTGGACTTGCATTGTTATTGATTTGGAAA
           G  E  C  I  C  G  Q  C                   I  G  L  A  L  L  L  I  W  K
```

PRIMER B3F  5' GGTGATTGTTTTGTGGTCAGTG 3'       PRIMER B4E  3' TAACCTGAACATCGTGATTACTATACCTT 5'
```
                     C   C   A                                       G  T  GG AA A C   G
                     C   C   C
                     G   G   G
```

PRIMER B3R  3' CTTACATAAACACCTGTCAC 5'
```
                        T        G
```

FIGURE 1B

β₆ PRIMERS

β₆ guinea pig  nt 219  CCATTGACAAATGATGCTGAAAGA
                       P  L  T  N  D  A  E  R PRIMER BTE2F          5' CCITTIACIAATGATGCIGAAAGA 3'
                                    C        C β₆ guinea pig  1325   CATCTCCGAAGACGGCA
                      I  S  E  D  G

PRIMER BTE3F          5' CATCTCCGAAGACGGCA 3'

```
β₆GP  AATGAATACTCCATGTCAACTGTCATGGAATATCCAACAATTGGACAACTCATTGATAAACAATGTTGTACAAAACAATGTGTACAAAACAATGTGTTACAAAACAATGTTGTTACTGATCTTTGCTGTAACCCAA    573
β₆H                                       M                                                                                                191
β₆GP  GAACAAGTTCATTTATATGAGAATTACGCAAAACTTATTCCTGGAGCTACACAGTTCTCACTTCAGAAGGACTCCGGAAACATTCTCCAGTCGATCATCTCA                                  1324
β₆H    E  Q  V  H  L  Y  E  N  Y  A  K  L  I  P  G  A  T  V  G  L  L  Q  K  D  S  G  N  I  L  Q  L  I  S                                  366
β₆GP  GAACAAGTTCCACTATATGAGAATTATGCAAAACTTATTCCGGAGCTACTTCAAGGACTTCCAAGGACTTCCAACTCGATCATCTCA                                               675
β₆H                                                                                              H                                          225
β₆GP  GCTTATGAAGAACTGCGGTCTGAGGTGGAACTGGAAGTATTAGGAGACACTGAAGGACTCAACTTGTCATTTACAGCCATCTGTAACAACGGTACCCTCTTC                                1426
β₆H    A  Y  E  E  L  R  S  E  V  E  L  E  V  L  G  D  T  E  G  L  N  L  S  F  T  A  I  C  N  N  G  T  L  F                              400
β₆GP  GCTTATGAAGAACTGCGCGTCTGAGGTGGACTGGAAGTATTAGGAGATACAGAGGGCCTCAATCTTTCGTTCTGAGCTGTCTGTAACAATGGCACTCTTC                                  777
β₆H                                                                                                                                          259
β₆GP  CAACACCAAAAGAAAATGCTCTCACATGAAAGTGGGAGACAGCTTCCTTCAGCGTGAATATCCCAGCGTGAATATCCCAGAGAAGAAGCAGCACATTATC                                  1528
β₆H    Q  H  Q  K  K  C  S  H  M  K  V  G  D  T  A  S  F  S  V  T  V  N  I  P  K  C  E  R  R  S  R  H  I  I                              434
β₆GP  CCACACCAAAAGAAATGCTTGCACATGAAATGAAAGTGGGAGATATCCATCAGCTTCATTCAATGAAAGTGAGTATACCAAACAGTTCAGGCATGTTATC                                 879
β₆H                               L                   E                       N                  S   N        K                            293
β₆GP  ATAAAGCCTGTGGGCTGGGGATGCGGCGTGTGTGCAGCCCTGGAATTACTTGTCAGCCCAGAATGCAACTGCGACTGTCAGAAATGAAGTGAACAGTTCCAAATGTCAC                         1630
β₆H    I  E  P  V  G  L  G  D  A  L  E  L  L  V  S  P  E  C  N  C  D  C  Q  K  E  V  E  V  N  S  S  K  C  H                              460
β₆GP  ATAAAGCCTGTGGGCTGGGGGACACAGTCTTGTCAGCCCAGAAATCCTTGTCAGCCCAGAAATGCAGCTGCGATTGTCAGAAAGAAGTGAAGTGAACAGTCCAAATGCCAC                       981
β₆H                                         S                                                            T       I                         327
β₆GP  CACGGGAACGGCTCTTCTTCCAGTGCTGTGGGGTCTGCGCTGCCCACACATGGGGGCCTGCCACCCGGGCCACATGTCGAGCGAGGACATGCTGAGCACAGATTCCTGC                        1732
β₆H    H  G  N  G  S  F  Q  C  G  V  C  A  C  H  P  G  H  M  G  P  R  C  E  C  G  E  D  M  L  S  T  D  S  C                              502
β₆GP  AATGGGAACGGCTCCTACCAGTGTGGGGTGTGTGCCTGTCACCCAGGCCACATGGGCCCCTCACTGCGAGTGTGGAGGACACGCTGAGCACAGATTCCTGC                                1883
β₆H                                                                                                                                          361
β₆GP  AAGGAGGCCCCAGATCATCCCTCCTGCAGCGGAAGGGGTGACTGCTACTGTGGGCAGTGTATCTGCCACTGTCTCCCTATGGAAACATTATGGACCTTAT                                 1834
β₆H    K  E  A  P  D  H  P  S  C  G  R  G  D  C  Y  C  G  Q  C  I  C  H  L  S  P  Y  G  N  I  Y  G  P  Y                                 536
β₆GP  AAGGAGACCCCAGACCCATCCTGTCGTGCAGCGGAAGGGGTGACTGCTACTGTGGGCAGTGCATCTGCCACTGTCTCCCTATGGAAACATTATGACCTTAC                                1185
β₆H                                                                                                                                          395
β₆GP  TGCCAGTGTGACAATTTCTCCTGCGTGAGGCACAAAGGCTGCTTCTGCGGAGGTAACGGCGAGTAACGCGGCGAGTAACGCGGCGAGTGTGTGCAGGAGCGGCTGGACT                        1936
β₆H    C  Q  C  D  N  F  S  C  V  R  H  K  G  L  L  C  G  G  N  G  D  C  D  C  G  E  C  V  C  R  S  G  W  T                              570
β₆GP  TGCCAGTGTGACAATTTCTCCTGTGTGAGGCACAAAGGCTGCTTCTGTGGAGATAACGGAGAGACTGTGAATGTGGGGGACTGTGAATGTGGAGAGTGTTGGACC                            1287
β₆H                                                                            D                                 B                          429
β₆GP  GGCGAGTACTGCAACTGCACCACCAGCACGGACTCCTGCGTCTCTGAAGATGGAGTGCTCTGCAGCGGCGGCGGGGACTGTGTTTGTGGCAAGTGTGTTTGC                                2838
β₆H    G  E  Y  C  N  C  T  S  T  D  S  C  V  S  E  D  G  V  L  C  S  G  R  G  D  C  V  C  G  K  C  V  C                                 604
```

FIGURE 3C

```
β₆GP GGAGAGTACTGCAACTGTACCACCAGCACACAGACACCTGCAGCTCCCGAAGACGGCACGCGGGGACTCGCTCTGTGGCAAGTGTGTCTGC    1389
                                                                                                463
β₆H  ACAAACCCTGGAGCCTCAGGACCTGTCACCTGTGAACGATGTCCTACCTGTGGTGACCCTGTAACTCTAAACGAGTGCCACCTGTCCAGCAGCT  2140
            T   N   P   G   A   S   G   P   T   C   E   R   C   P   T   C   G   D   P   .   C   N   S   K   R   S   C   I   E   C   H   L   S   A   A     638
                   T                                                   T                                                                                    
β₆GP ACGAACCCTGGAGCCTCGGGACCCGTGAACGATGTCCACCTGTGAACGATGTCCTACCTGTAACTCTAAACGAGCTCATTGAATGCCACCTGTCTGCAGAT  1491
                                                                                                            D  497
β₆H  GGCCAAGCCCGGAGAAGAATGTGGACAAGTGCAAACTAGCTGGTGCGACCATCAGTGAAGAAGAAGATTCTCAAAGGATGGTTCTGTTCCTGCTCTG    2242
            G   Q   A   G   E   E   C   V   D   K   C   K   L   A   G   A   T   I   S   E   E   E   D   F   S   K   D   G   S   V   S   C   S   L     672
                                                                          V   K       A               S                                                    
β₆GP GGTCAGCCTGGAGAAGAATGTGTGGACAAGTGTGGACAATCAGCAGGTGTGACCATCAGCAAGTAGCCAAAGAACAGATTTCTCAAAGGATAGTTCGTTCCTGCTCCTG  1583
            G   V   S   L   E   K   N   V   V   D   K   V   G   Q   S   A   G   V   T   I   S   K           P                                    531
β₆H  CAAGGAGAAAATGAATGTTTAATTACATTCCTAATTACTACAGATAATGAGGGGAAAAACCATCATTCACAGATCAATGAAAAAGATTGTCCGAAGCCTCCA    2344
            Q   G   E   N   E   C   L   I   T   F   L   I   T   T   D   N   E   G   K   T   I   H   S   I   N   E   K   D   C   P   K   P   P     706
β₆GP CAAGGAGAAAATGAATCATTGAATTGTCTTATTACATTCCTAATTAGTACAGATAATGAGGGAAAAACATCAGTGAACATCAATGACTGCCCAAACCTCA  1695
                                                                                                            565
β₆H  AACATTCCCATGATCATGTTAGGGGTTCCCTGGCACTCTTCTCTCATGGGGTTGTCCTACTGTGCATCTGAAGCTCGTGTCATTCATGATCGTAAA  2446
            N   I   P   M   I   M   L   G   V   S   L   A   T   L   L   I   G   V   V   L   L   C   I   W   K   L   L   V   S   F   N   D   R   K     740
                                                          S                                       N       S                                                
β₆GP AATATTCCTATGATCATGTTGGGGGTTTCACTGGCTA                                                            1732
                                                                                                            577
β₆H  GAAGTTGCCAAATTGAAGCAGAACGATCAAAAGCCAAGTGGCAAACGGAACCAATCCACTCTACAGAGGATCCACAAGTACTTTAAAAATGTAACTTAT  2548
            E   V   A   K   F   E   A   E   R   S   K   A   K   W   Q   T   G   T   N   P   L   Y.  R   G   S   T   F   K   N   V   T   Y     774
β₆H  AAACAGGGAAAAACAAAAGGTAGACCTTTCCACAGATTGCTAGAACTACTTTATGCATAAAAAAGTCTGTTTCACTGATGAAATGTTAATG             2644
            K   H   R   E   K   Q   K   V   D   L   S   T   D   C                                                                                    788
```

FIGURE 4A

```
β1     human        MNLQPIFWIGLISSVCCVFAQT
β2     human        MLGLRPPLLALVGLLSLGCV
β3     human        MRARPRPLMVTVLALGALAGVGVG
βmyo   Drosophila   MILERNRRCQLALLMIAMLAAIAAQTNAQKAAKLT
β6     human        MGIELLCLFFLFLGRNDSR
                    *                        *

β1   DENRCLKANAKSCGECIQAGPNCGWCTNSTFFQEMPTSARCDDLEALKKKGCPPDDIENPRGSKDIKKNKNVTNRSKGTAEKLKPEDIHQ         112
β2   LSQECTKFKVSSCRECIESGPGCTWCQKLNFTGPGDPDSIRCDTRPQLLMRGCAADDIMDPTSLAETQEDHNG                GQKQ      96
β3   GPNICTTRGVSSCQQCLAVSPMCAWCSDEAL    PLGSPRCDLKENLLKDNCAPESIEFPVSEARVLEDRPL  SDKGSGDSS     QVTQ      107
βmyo AVSTCA  SKEKCHTCIQTE  GCAWCMQPDF      KGQS RC Y QN TSSLCPEEFAYSPITVEQILVNNKLTNQYKAE insert IVQ    137
β6   TRWLCLG GAETCEDCLLIGPQCAWCAQENFTHPSGVGE RCDTPANLLAKGCQLNFIENPVSQVEILKNKPL  SVGRQKNSS     DIVQ      108
             *                   *

β1   IQPQQLVLRLRSGEPQTFTLKFKRAEDYPIDLYYLMDLSYSMKDDLENVKSLGTDLMNEMRRITSDFRIGFGSFVEKTVMPYISTTPAK L         202
β2   LSPQKVTLYLRPGQAAAFNVTFRRAKGYPIDLYYLMDLSYSMLDDLRNVKKLGGDLLRALNEITESGRIGFGSFVDKTVLPFVNTHPDK L         186
β3   VSPQRIALRLRPDDSKNFSIQVRQVEDYPVDIYYLMDLSYSMKDDLWSIQNLGTKLATQMRKLTSNLRIGFGAFVDKPVSPYMYISPPEAL         198
βmyo IQPQSMRLALRVNEKHNIKISYSQAEGYPVDLYYLMDLSKSMEDDKAKLSTLGDKLSETMKRITNNFHLGFGSFVDKVLMPYVSTIPKK L         227
β6   IAPQSLILKLRPGGAQTLQVHVRQTEDYPVDLYYLMDLSASMDDDLNTIKELGSSGLSKEMSKLTSNFRLGFGSFVEKPVSPFVKTTPEE I         193
                             ---B1---- 
                                                       *

β1   RNPC TSEQNCTTPFSYKNVLSLITNKGEVFNELVGKQRISGNLDSPEGGFDAIMQVAVCGSLIGWRN VTRLLVFSTDAGFHFAGDGKLGG        291
β2   RNPCPNKEKECQPPFAFRHVLKLITNNSNQFQTEVGKQLISGNLDAPEGGLDAMMQVAACPEEIGWRN VTRLLVFATDDGFHFAGDGKLGA        276
β3   ENPCYDMKTCLPMFGYKHVLTLTDQVTRFNEEVKKQSVSRNRDAPEGGFDAIMQATVCDEKIGWRNDASHLLVFTTDAKTHIALDGRLAG        289
βmyo EHPC  ENCKAPYGYQNHMPLNNTESFSNEVKNATVSGNLDAPEGGFDAIMQAIACRSQIGWREQARRLLVFSTDAGFHYAGDGKLGG           314
β6   ANPCSSIPYFCLPTFGFKHILPLTNDAERFNEIVKNQKISANIDTPEGGFDAIMQAAVCKEKIGWRNDSLHLLVFVSDADSHFGMDSKLAG        282
                              ---B2---
```

FIGURE 4B

```
                                                                                                    *
β₁     IVLPNDGQCHLENNM  YTMSHYYDYPSIAHLVQKLSENNIQTIFAVTEEFQPVYKELKNLIPKSAVGTLSANSSNVIQLIIDAYNSLSSEV    381
β₂     ILTPNDGRCHLEDNL  YKRSNEFDYPSVGQLAHKLAENNIQPIFAVTSRMVKTYEKLTEIIPKSAVGELSEDSSNVVHLIKNAYNKLSSRV    366
β₃     IVQPNDGQCHVGSDNHYSASTTMDYPSLGLMTEKLSQKNINLIFAVTENVVNLYQNYSELIPGTTVGVLSMDSSNVLQLIVDAYGKIRSKV      380
βmyo   VIAPNDGECHLSPKGEYTHSTLQDYPSISQINQKVKDNAINIIFAVTASQLSVYEKLVEHIQGSSAAKLDNDSSNVVELVKEEYRKISSSV      405
β₄     IVIPNDGLCHLDSKNEYSMSTVLEYPTIGQLIDKLVQNNVLLIFAVTQEQVHLYENYAKLIPGATVGLLQKDSGNILQLIISAYEELRSEV      375

*  *   *
β₁     ILENGKLSEGVTISYKSYCKNGVNGTGENGRKCSNISIGDEVQFEISITSNKCPKK  D    SDSFKIRPLGFTEEVEVILQYICECECQSEG  469
β₂     FLDHNALPDTLKVTYDSFCSNGVTHRNQPRGDDGVQINVPITFQVKVTATECIQE   Q       SFVIRALGFTDIVTVQVLPQCECRCRDQS  452
β₃     ELEVRDLPEELSLSFNATCLNNEVIPGL   KSCMGLKIGDTVSFSIEAKVRGCPQE K    EKSFTIKPVGFKDSLIVQVTFDCDCACQAQA  466
βmyo   EMKDNATGD VKITYFSSCLSNGPEVQT    SKCDNLKEGQQVSFTAQIQLLKCPEDPRDWTQTIHISPVGINEVMQIQLTMLCSCPCENPG    493
β₄     ELEVLGDTEGLNLSFTAICNNGTLFQHQ    KKCSHMKVGDTASFSVTVNIPHC  ER   R   SRHIIKPVGLGDALELLVSPECNCDCQKEV  460

*                                                                *
β₁     I   PESPKCHEGNGTFECGACRCNEGRVGRHCECSTDEVN SEDM DAYCRKENSS  EICSNNGECVCGQCVCKRDNTNEIYSGKFCE      553
β₂     R   DRSLCH GKGFLECGICRCDTGYIGKNCECQTQGRS SQEL EGSCRKDNNS  IICSGLGDCVCGQCLCHTSDVPGKLIYGQYCE      534
β₃     E   PNSHRCNGNGTFBCGVCRCGPGMLGSQCBCSEEDYRPSQQ DE CSPREGQ   PVCSQRGECLCGQCVCHSSDF GKIT GKYCE      547
βmyo   SIGYQVQANSCS GHGTESMCGICNCDDSYFGNKCECSATDLT  SKFANDTSCRADTSTSTDCSGRGHCVCGACECHKRPNPIEIISGKHCE   582
β₄     E   VNSSKCHHGNGSFQCGVCACHPGHMG PRCECGEDML  ST  D  SCKEAPDH PSCSGRGDCYCGQCICHLSPY GN IYGPYCQ      538
                                                                        ---B3---
                                                                  *              *
β₁     CDNFNCDRSNGLICGG  NGVCKCRVCECNPNYTGSACDCSLDTSTCEASN GQICNGRGICECGVCKCT    DPKFQGQTCEMCQTCLGV   638
β₂     CDTINCERYNGOVCGGPGRGLCFCGKCRCHPGFEGSACQCERTTEGCLNPR RVECSGRGRCRCNVCECH    SG YQLPLCQECPGCPSP    620
β₃     CDDFSCVRYKGEMCSG  HGQCSCGDCLCDSDWTGYYCNCTTRTDTCMSSN GLLCSGRGKCECGSCVCI    QPGSYGDTCEKCPTCPDA    632
βmyo   CDNFSCERNRNQLCSGPDHGTCECGRCKCKPGWTGSNCGCQESNDTCMPPGGGEICSGHGTCECGVCKCTVNDQGRFSGRHCEKCPTCSGR   673
β₄     CDNFSCVRHKGLLCGG  NGDCDCGECVCRSGWTGEYCNCTTSTDSCVSED GVLCSGRGDCVCGKCVCT    NPGASGPTCERCPTCGDP    623
```

FIGURE 4C

```
              *              *                      *                        *                                  *
β₁   CAEHKECVQCRAFNKGE  KKDTCTQECSYFNITKVESRDKLPQPVQPDPVSHCKEKDVDDCWFYFTY  SVNGNNEVMVHVVENPECPTGP     726
β₂   CGKYISCAECLKFEKGPF  GKNCSAACPG     LQLSW  NPVKGRT CKERDSEGCWVAYTLE  QQDGMDRYLIYVDESRECVAGP     698
β₃   CTFKKECVECKKFDREPYMTENTCNRYCRDEIESVKELKD           TGKDAVN CTYKNEDDCVVRFQY  YEDSSGKSILYVVEEPECPKGP     715
βmyo CQELKDCVQCQMYKTGELKNGDDCARNCTQFVPVGVEKVEID         ETKDEQM CKFFDEDDCKFMFKY        SEQGELHVYAQENKECPAKV     757
β₆   CNSKRSCIECHLSAAGQA  GEECVDKCKLAGATISEEEDF         SKDGSVS CSLQGENECLITFLI  TTDNEGKTIIHSINEKDCPKPP     706

β₁   DIIPIVAGVVAGIVLIGLALLIWKLMIIHDRREFAKFEKEKMNAKWDTGENPIYKSAVTTVVNPKYEGK                              797
β₂   NIAAIVGGTVAGIVLIGILLLVIWKALIHLSDLREYRRFEKEKLKSQWNN DNPLFKSATTTVMNPKFAES                            769
β₃   DILVVLLSVMGAILLIGLAALLIWKLLITIHDRKEFAKFEEERARAKWDTANNPLYKEATSTFNITYRGT                             786
βmyo FMLGIVMGVIAAIVLVLGLAILLLMKLLTTIHDRREFARFEKERMNAKWDTGENPIYKQATSTFKNPMYAGK                           828
β₆   NIPMIMLGVSLATLLIGVVLLCIWKLLVSFHDRKEVAKFEAERSKAKWQTGTNPLYRGSTSTFKNVTYKHREKQKVDLSTDC                 788

```
β3GP  ATGTCCAGCAACGGGCTGTTGTGCAGCGGGCCCGGGAAGTGTGAATGTGGCAGTTGTGTCTGCATCCAGCCGGATCTTATGGGACACTC
β6H   GTCTCTGAAGATGGAGTGCTCTGCAGCGGGCGGGGACTGTGTTGTGGCAAGTGTGTTGCACAAACCCTGGAGCCTCAGAGCCTCAGACCAACC
       V  S  E  D  G  V  L  C  S  G  R  G  D  C  V  C  G  K  C  V  C  T  N  P  G  A  S  G  P  T
β6GP  ATCTCCGAAGACGGCACGCTCTGCAGCGGCGGCGGGGACTGTGTCTGTGGCACTGTCTGTGGCAAGTGTCTCTGCGACGAACCCTGGAGCCTCGGAGCCTCGGGACCCACC
       I                                                                T
```

US 6,787,322 B2

METHODS OF EXPRESSING INTEGRIN $\beta_6$ SUBUNITS

CROSS REFERENCE TO RELATED APPLICATIONS

This application is a continuation application of U.S. patent application Ser. No. 10/072,841, filed Feb. 6, 2002, which is a continuation of U.S. patent application Ser. No. 09/591,543, filed Jun. 8, 2000, now abandoned which is a divisional application of U.S. patent application Ser. No. 08/938,085, filed Sep. 26, 1997, now U.S. Pat. No. 6,339,148, which is a divisional application of U.S. patent application No. 07/728,215, filed Jul. 11, 1991, now U.S. Pat. No. 5,962,643 each of which is incorporated herein by reference.

This work was supported in part by research grants HL/AL 33259, CA-47541 and CA-47858 from the National Institutes of Health. The U.S. Government has rights in the invention.

BACKGROUND ART

This invention relates to receptors for adhesion peptides, and more specifically to a novel receptor subunit having affinity for extracellular matrix molecules.

Multicellular organisms, such as man, have some $10^{14}$ cells which can be divided into a minimum of fifty different types, such as blood cells and nerve cells. During the course of growth and development, cells adhere to other cells, or to extracellular materials, in specific and orderly ways. Such cell adhesion mechanisms appear to be of importance in mediating patterns of cellular growth, migration and differentiation, whereby cells develop specialized characteristics so as to function as, for example, muscle cells or liver cells. Cell adhesion mechanisms are also implicated in dedifferentiation and invasion, notably where cells lose their specialized forms and become metastasizing cancer cells.

The mechanisms underlying the interactions of cells with one another and with extracellular matrices are not fully understood, but it is thought that they are mediated by cell surface receptors which specifically recognize and bind to a cognate ligand on the surface of cells or in the extracellular matrix.

The adhesion of cells to extracellular matrices and their migration on the matrices is mediated in many cases by the binding of a cell surface receptor to an Arg-Gly-Asp containing sequence in the matrix protein, as reviewed in Ruoslahti and Pierschbacher, Science 238:491–497 (1987). The Arg-Gly-Asp sequence is a cell attachment site at least in fibronectin, vitronectin, fibrinogen von Willibrand, thrombopondin, osteopontin, and possibly various collagens, laminin and tenascin. Despite the similarity of their cell attachment sites, these proteins can be recognized individually by their interactions with specific receptors.

The integrins are a large family of cell surface glycoproteins that mediate cell-to-cell and cell-to-matrix adhesion as described, for example, in the Ruoslahti and Pierschbacher article cited above. All known members of this family of adhesion receptors are heterodimers consisting of an $\alpha$ and a $\beta$ subunit noncovalently bound to each other. When the integrin family was first identified, integrins were grouped into three subfamilies based on the three $\beta$ subunits that were initially recognized ($\beta_1$, $\beta_2$ and $\beta_3$). Over the past few years, the primary structures of three integrin $\beta$ subunits from mammalian cells and one from Drosophila have been deduced from cDNA.

Each $\alpha$ subunit was thought to associate uniquely with a single $\beta$ subunit. Eleven distinct $\alpha$ subunits have thus far been described. As new integrins have been identified, however, it has become clear that this grouping is not entirely satisfactory, since there are clearly more than three $\beta$ subunits and since some $\alpha$ subunits can associate with more than one $\beta$ subunit as described, for example, in Sonnenberg et al., J. Biol. Chem. 265:14030–14038 (1988).

Because of the importance of integrins in mediating critical aspects of both normal and abnormal cell processes, a need exists to identify and characterize different integrins. The present invention satisfies this need and provides related advantages as well.

SUMMARY OF THE INVENTION

The present invention relates to a substantially purified $\beta$ subunit of an integrin cell surface receptor designated as $\beta_6$. The amino acid sequence of human $\beta_6$ (SEQ ID NO:27) is provided in FIG. 3.

The present invention also relates to amino acid fragments specific to $\beta_6$ that have a variety of uses. The invention further relates to vectors having a gene encoding such fragments. Host cells containing such vectors are also provided. The nucleic acids encoding $\beta_6$ as well as nucleic acids that specifically hybridize with the nucleic acids encoding $\beta_6$ sequences are other aspects of the present invention.

In a further aspect, the present invention relates to a substantially purified integrin comprising $\beta_6$ bound to an $\alpha$ subunit, particularly $\alpha_V$ or $\alpha_F$. Methods of blocking the attachment of the $\beta_6$-containing integrins to its ligand and of detecting the binding of such integrins to its ligand are also provided.

The present invention also relates to methods of increasing or decreasing cell adhesion in cells expressing a $\beta_6$-containing integrin by overexpressing the integrin or by binding the integrin with a ligand, such as vitronectin.

BRIEF DESCRIPTION OF THE FIGURES

FIG. 1 shows the design of consensus PCR primers (SEQ ID NOS:1–5, 7 and 8)($\beta_2$ human nucleic acids=SEQ ID NOS:10, 14, 18 and 22; corresponding $\beta_2$ human amino acids=SEQ ID NOS:50, 51, 54 and 55; $\beta_3$ human nucleic acids=SEQ ID NOS:11, 15, 19 and 23; corresponding $\beta_3$ human amino acids=SEQ ID NOS:52, 53, 56 and 57; $\beta_1$ human nucleic acids=SEQ ID NOS:12, 16, 20 and 24; corresponding $\beta_1$ human amino acids=SEQ ID NOS:50, 53, 58 and 59; $\beta_1$ chicken nucleic acids=SEQ ID NOS:13, 17, 21 and 25; corresponding $\beta_1$ chicken amino acids SEQ ID NOS:50, 53, 60 and 59; $\beta_6$ guinea pig sequence from position 219=SEQ ID NO:6; corresponding $\beta_6$ guinea pig amino acids=SEQ ID NO:61; $\beta_6$ guinea pig sequence from position 1325=SEQ ID NO:8; corresponding 136 guinea pig amino acids=SEQ ID NO:62).

FIG. 3 shows the nucleotide sequence and amino acid translation for human (H) (SEQ ID NOS:26 and 27) and guinea pig (GP) (SEQ ID NOS:28 and 29).

FIG. 4 shows the alignment of human $\beta_6$ (SEQ ID NO:27) with, four previously reported integrin $\beta$ subunits (human $\beta_1$=SEQ ID NO:30; human $\beta_2$=SEQ ID NO:31; human $\beta_3$=SEQ ID NO:32; Drosophila $\beta_{myo}$=SEQ ID NO:33).

FIG. 5 shows the alignment of partial nucleotide and amino acid sequences from human (H) and guinea pig (GP) $\beta_1$ (human ($\beta_{3H}$)=SEQ ID NOS:34 and 35; guinea pig ($\beta_{1GP}$)=SEQ ID NOS:36 and 37, respectively), $\beta_3$ (human ($\beta_{1H}$)=SEQ ID NOS:38 and 39; guinea pig ($\beta_{3GP}$)=SEQ ID NOS:40 and 41, respectively), and $\beta_6$ (human ($\beta_{6H}$)=SEQ ID NOS:42 and 43; guinea pig ($\beta_{6GP}$)=SEQ ID NOS:44 and 45, respectively) for the region just downstream from the B3F primer.

DETAILED DESCRIPTION OF THE INVENTION

Figure 2:
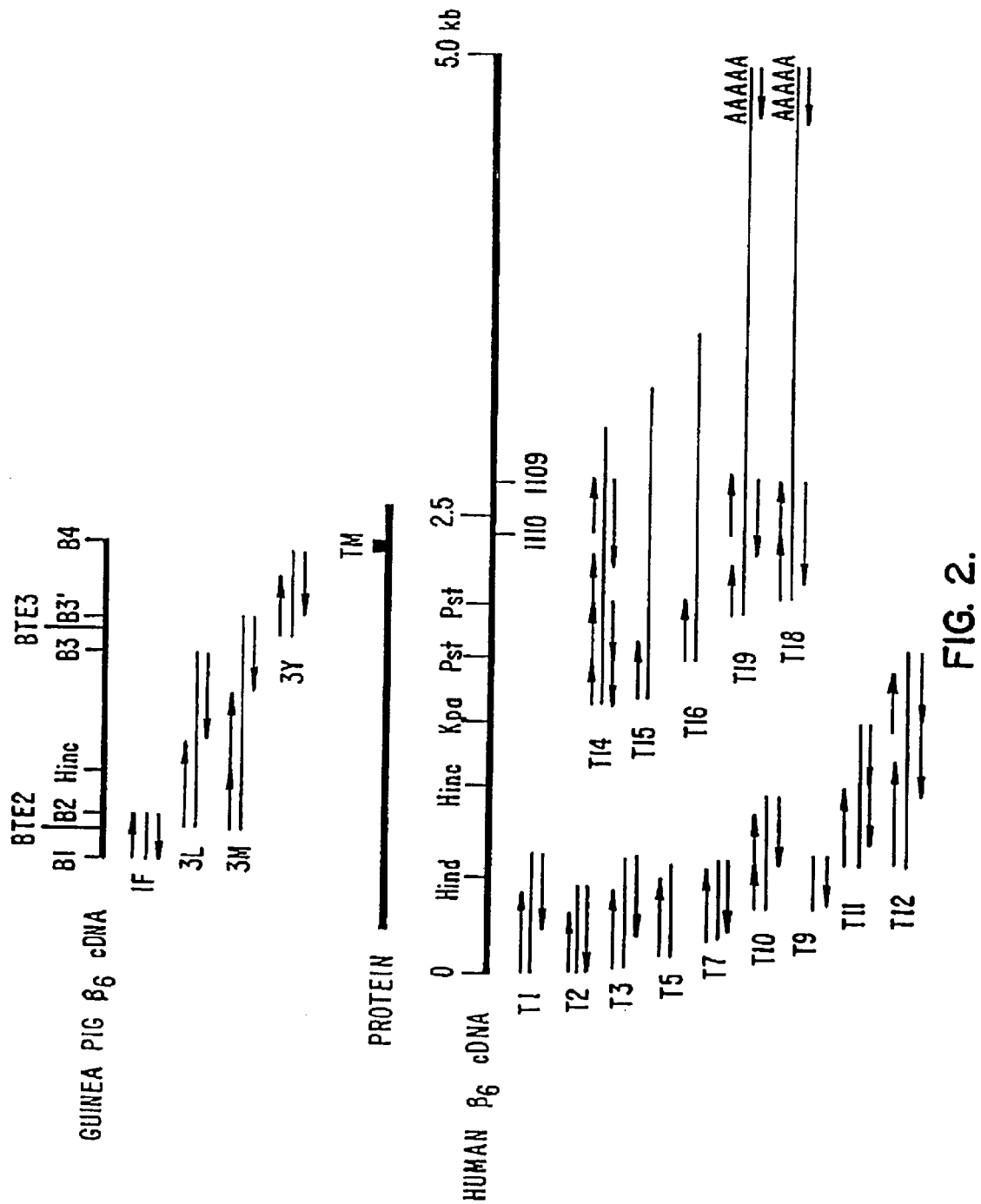
FIG. 2 shows a map of sequencing strategy.

The present invention provides a composition of matter relating to a novel, substantially purified integrin β subunit, referred to herein as $\beta_6$. The amino acid sequence of $\beta_6$ for humans (SEQ ID NO:27) and for guinea pig (SEQ ID NO:29) are also provided and are shown in FIG. 3.

By "substantially purified" is meant substantially free of contaminants normally associated with a native or natural environment.

By "$\beta_6$" is meant a polypeptide having substantially the same amino acid sequence and binding functions of the polypeptides encoded by the sequences set forth in FIG. 3 for human (SEQ ID NO:26) and guinea pig (SEQ ID NO:28)$\beta_6$. Thus, modified amino acid sequences that do not substantially destroy the functions and retain the essential sequence of $\beta_6$ are included within the definition of $\beta_6$. Amino acid sequences, such as the sequence for $\beta_1$ (SEQ ID NO:30), β2 (SEQ ID NO:31), and $\beta_3$ (SEQ ID NO:32), having less than 50% homology with the sequence of $\beta_6$, are not substantially the same sequence and, therefore, do not fall within the definition of $\beta_6$. Given the amino acid sequences set forth herein, additions, deletions or substitutions can be made and tested to determine their effect on the function of $\beta_6$. In addition, one skilled in the art would recognize that certain amino acids, such as the conserved cystines, for example, can be modified to alter a binding function of $\beta_6$.

Amino acids are identified herein by the standard one-letter abbreviations, as follows:

| Amino Acid | Symbol |
| --- | --- |
| Alanine | A |
| Asparagine | N |
| Aspartic acid | D |
| Arginine | R |
| Cysteine | C |
| Glutamine | Q |
| Glutamic acid | E |
| Glycine | G |
| Histidine | H |
| Isoleucine | I |
| Leucine | L |
| Lysine | K |
| Methionine | M |
| Phenylalanine | F |
| Proline | P |
| Serine | S |
| Threonine | T |
| Tryptophan | W |
| Tyrosine | Y |
| Valine | V |

Based on its amino acid sequence, the β subunit of the present invention is clearly different from $\beta_1$, $\beta_2$, $\beta_3$ and other β subunits that have recently been discovered. For example, the 11-amino acid carboxyl-terminal extension on $\beta_6$ distinguishes it from $\beta_1$, $\beta_2$, and $\beta_3$. The short cytoplasmic tails of $\beta_1$, $\beta_2$, and $\beta_3$ are thought to be sites of interaction with the cytoskeleton and regions for the transduction of signals initiated by interactions of the large extracellular domains with ligands. These cytoplasmic tails may also be targets for regulation of integrin function. The distinctive 11-amino acid cytoplasmic tail of $\beta_6$ indicates that its regulation or pathways for signal transduction may be different from those of $\beta_1$, $\beta_2$ and $\beta_3$.

In addition to $\beta_1$, $\beta_2$ and $\beta_3$ recent studies have suggested the existence of as many as five other integrin β subunits. A β subunit with a molecular weight of approximately 210,000 ($\beta_4$) has been found associated with the integrin a subunit "$\alpha_6$" in colon carcinoma cells and in a variety of other tumor cells of epithelial origin as described, for example, in Kajiji et al., *EMBO J.*, 8:673–680 (1989). On the basis of its high molecular weight, 210,000 compared with the predicted size of 106,000 of the subject novel protein, and on the basis of its clearly different amino-terminal sequence, it is apparent that $\beta_4$ is not the same as the subject polypeptide.

Another β subunit, originally called $\beta_x$ was identified in epithelial-derived tumor cells in association with the integrin α subunit $\alpha_V$ as described, for example, in Cheresh et al., *Cell* 57:59–69 (1989). This β subunit, having a distinctive amino-terminal sequence, was recently renamed $\beta_5$. Based on recent studies of purified preparations, $\beta_5$ clearly differs from the β subunit of the present invention. Because the β subunit described in the present report is distinct from each of the five β subunits for which sequence information is available, it has been designated as $\beta_6$.

The existence of two other integrin β subunits has been inferred from the identification of unique proteins after immunoprecipitation of surface-labeled cell lysates with antibodies to known α subunits. One of these novel proteins, called $\beta_S$ was found in association with $\alpha_V$ in the human osteosarcoma cell line MG-63, in the fibroblast cell line AF1523, and in human endothelial cells as described, for example, in Freed et al., *EMBO J.*, 8:2955–2965 (1989). This subunit is also different from $\beta_6$ since $\beta_S$ is expressed in MG-63 cells while $\beta_6$ is not expressed in these cells as shown in Table 1.

The other novel integrin β subunit identified by co-immunoprecipitation of known α subunits, $\beta_P$, is a protein of about $M_r$ 95,000 that is found to be associated with $\alpha_4$, an α subunit first found as part of the lymphocyte homing receptor VLA-4 as described, for example, in Holzmann et al., *Cell* 45:37–46 (1989). This subunit is also distinct from $\beta_6$ since $\beta_P$ is expressed in lymphocytes while $\beta_6$ is not expressed in lymphocytes as shown in Table 1.

TABLE 1

Distribution of $B_6$

| Cell Lines: | Type | Results | Source |
| --- | --- | --- | --- |
| FG-2 | Pancreatic | + | Kajiji et al., EMBOJ. 3:673–80 (1989) |
| Panc I | Pancreatic | – | Dr. Metzgar, Duke U., N.C. |
| Colo-396 | Colon CA | + | Dr. L. Walker, Cytel, San Diego, CA |
| UCLA P3 | Lung CA | + | Dr. L. Walker, Cytel, San Diego, CA |
| HeLa | Cervical | – | ATCC #CCL-2 |
| Jar | Chorio CA | + | ATCC #HTB 36 |
| HT 1080 | Fibrosarcoma | – | ATCC #CCL 121 |
| U 937 | Monocytoid | – | ATCC #CRL 1593 |
| M 21 | Melanoma | – | Dr. R. Reisfeld, Scripps Clinic & Research Foundation, La Jolla, CA |

TABLE 1-continued

Distribution of $B_6$

| Cell Lines: | Type | Results | Source |
|---|---|---|---|
| B 16 | Melanoma | − | Dr. R. Reisfeld Scripps Clinic & Research Foundation, La Jolla, CA |
| MG 63 | Osteosarcoma | − | ATCC #CRL 1427 |
| Tissues: | Cervix | + | |
| | Aortic Endothelium | − | |
| | Leukocytes | − | |

The invention also provides an integrin comprising $\beta_6$ bound to an $\alpha$ subunit. $\beta_6$, consistent with recent findings of other $\beta$ subunits, can associate with a variety of $\alpha$ subunits to form a functional integrin. In one embodiment, $\beta_6$ associates with $\alpha_V$. In another embodiment, $\beta_6$ associates with another $\alpha$ subunit referred to herein as $\alpha_F$. The $\alpha_V \beta_6$ integrin, as well as other integrins containing $\beta_6$, can bind molecules, for example extracellular matrix molecules. Such molecules are referred to herein as ligands. In a specific embodiment, certain $\beta_6$-containing integrins can bind Arg-Gly-Asp-containing polypeptides such as vitronectin or fibronectin. The binding of $\beta_6$-containing integrins to various ligands can be determined according to procedures known in the art and as described for example, in Ruoslahti and Pierschbacher, Science 238:491–497 (1987).

The invention also provides an amino acid fragment specific to $\beta_6$. Since $\beta_6$ is a novel molecule, it contains many fragments which are specific for this $\beta$ subunit. Fragments specific to $\beta_6$ contain sequences having less than 50% homology with sequences of other known integrin $\beta$ subunit fragments. These fragments are necessarily of sufficient length to be distinguishable from known fragments and, therefore, are "specific for $\beta_6$." The amino acid sequence of such fragments can readily be determined by referring to the figures which identify the $\beta_6$ amino acid sequences. These fragments also retain the binding function of the $\beta_6$ subunit and can therefore be used, for example, as immunogens to prepare reagents specific for $\beta_6$ or as an indicator to detect the novel $\beta_6$-containing integrin of the present invention. One skilled in the art would know of other uses for such fragments.

The invention also provides a reagent having specificity for an amino acid sequence specific for $\beta_6$. Since $\beta_6$ is a novel protein with at least 50% amino acid differences over related $\beta$ subunits, one skilled in the art could readily make reagents, such as antibodies, which are specifically reactive with amino acid sequences specific for $\beta_6$ and thereby immunologically distinguish $\beta_6$ from other molecules. Various methods of making such antibodies are well established and are described, for example, in Antibodies, A Laboratory Manual, E. Harlow and D. Lane, Cold Spring Harbor Laboratory 1988, pp. 139–283 and Huse et al., Science 24:1275–1280 (1988).

The invention also provides nucleic acids which encode $\beta_6$. Examples of such sequences are set forth in FIG. 3 (SEQ ID NOS:26 and 28). Following standard methods as described, for example, in Maniatis et al., Molecular Cloning, Cold Spring Harbor (1982), nucleic acid sequences can be cloned into the appropriate expression vector. The vector can then be inserted into a host, which will then be capable of expressing recombinant proteins. Thus, the invention also relates to vectors containing nucleic acids encoding such sequences and to hosts containing these vectors.

The sequences set forth in FIG. 3 (SEQ ID NOS:26 and 28) also provide nucleic acids that can be used as probes for diagnostic purposes. Such nucleic acids can hybridize with a nucleic acid having a nucleotide sequence specific for $\beta_6$ but do not hybridize with nucleic acids encoding non-$\beta_6$ proteins, particularly other cell surface receptors. These nucleic acids can readily be determined from the sequence of $\beta_6$ and synthesized using a standard nucleic acid synthesizer. Nucleic acids are also provided which specifically hybridize to either the coding or non-coding DNA of $\beta_6$.

Integrin cell surface receptors bind ligands, such as extracellular matrix molecules. However, the binding of the integrin to the ligand can be blocked by various means. For example, the binding of a $\beta_6$-containing integrin can be blocked by a reagent that binds the $\beta_6$ subunit or the $\beta_6$-containing integrin. Examples of such reagents include, for example, Arg-Gly-Asp-containing peptides and polypeptides, ligand fragments containing the integrin binding site, as well as antibodies specifically reactive with $\beta_6$ or a $\beta_6$-containing integrin. Alternatively, the blocking can be carried out by binding the ligand or fragment thereof, recognized by a $\beta_6$-containing integrin with a reagent specific for the ligand at a site that inhibits the ligand from binding with the integrin. Since the binding of a $\beta_6$-containing integrin to its ligand can mediate cell adhesion to an extracellular matrix molecule, preventing this binding can prevent cell adhesion. Alternatively, cell adhesion can be promoted by increasing the expression of $\beta_6$-containing integrins by a cell.

Finally, the invention provides a method of detecting ligands which bind a $\beta_6$-containing integrin. The method comprises contacting a $\beta_6$-containing integrin with a solution containing ligands suspected of binding $\beta_6$-containing integrins. The presence of ligands which bind a $\beta_6$-containing integrin is then detected.

The following examples are intended to illustrate but not limit the invention.

EXAMPLE I

Identification of a Novel $\beta$ Subunit

A. Generation of cDNA Fragments by Polymerase Chain Reaction

Tracheal epithelial cells, harvested from male Hartley outbred guinea pigs (Charles River Breeding Laboratories, Bar Harbor, Me.) were grown to confluence over 10–14 days on collagen-impregnated microporous filters commercially available from Costar. RNA was harvested from these primary cultures, and mRNA was purified over oligo(dT)-cellulose columns using the Fast Track mRNA isolation kit (Invitrogen, San Diego, Calif.). Two to 5 μg of mRNA was used as a template for cDNA synthesis catalyzed by 200 units of Moloney murine leukemia virus reverse transcriptase (Bethesda Research Laboratories, Gaithersburg, Md.) in a 20–40 μl reaction volume. One to 5 μl of the resultant cDNA was used as a template for polymerase chain reaction (PCR). PCR was carried out in a reaction volume of 25–200 μl. In addition to the template cDNA, each PCR reaction contained 50 mM KCl, 10 mM Tris-HCl (pH 9.0 at 25° C.), 1.5 mM $MgCl_2$, 0.01% gelatin, 0.1% Triton X-100, 0.2 mM each of dATP, dGTP, dCTP and dTTP, and 0.05 units/μl Taq DNA polymerase (obtained from either United States Biochemical Corporation, Cleveland, Ohio, or from Promega, Madison, Wis.).

For each reaction, two oligonucleotide primers were also added to obtain a final concentration of 1 μM each. The primer pairs are identified below. Each reaction mixture was overlaid with mineral oil, heated to 95° C. for 4 min. in a thermal cycler (Ericomp, San Diego, Calif.), and then subjected to 30 cycles of PCR. Each cycle consisted of 45 seconds at 95° C., 45 seconds at 53° C., and 1 min. at 72° C. Immediately after the last cycle, the sample was maintained at 72° C. for 10 min.

The results of each PCR reaction were analyzed by gel electrophoresis in 1.5% agarose. Reactions that produced fragments of the expected size were electrophoresed in 1.5% low gel temperature agarose (Bio-Rad Laboratories, Richmond, Calif.). The appropriate size band was excised, melted at 68° C., and the DNA was purified by extraction with phenol/chloroform and precipitation in ethanol and ammonium acetate.

B. PCR Primers

To obtain the initial fragment of the novel β subunit cDNA described herein, degenerate mixtures of PCR primers were used. Oligonucleotides were synthesized, trityl-on, by the University of California, San Francisco Biomolecular Resource Center using a DNA synthesizer with standard procedures, and purified over Nen-sorb cartridges (DuPont-New England Nuclear, Boston, Mass.). These consensus primer mixtures were designed to anneal with the nucleotides encoding the highly conserved sequence Asp-Leu-Tyr-Tyr-Leu-Met-Asp-Leu (SEQ ID NO:50) (primer B1F) (SEQ ID NO:1) and Glu-Gly-Gly-Phe-Asp-Ala-Ile-Met-Gln (SEQ ID NO:53) (primer B2R) (SEQ ID NO:2) that flank an approximately 300-nucleotide region beginning approximately 130 amino acids from the amino terminus of each of the integrin β subunits sequenced to date. The sequences of the primers identified herein are depicted in FIG. 1 (SEQ ID NOS:1–8).

On the basis of the initial sequence obtained, a specific forward primer was designed to anneal with the sequence encoding the amino acids Pro-Leu-Thr-Asn-Asp-Ala-Glu-Arg (SEQ ID NO:61) (primer BTE2F) (SEQ ID NO:7) ending approximately 49 nucleotides from the 3' end of the region that had been sequenced. An additional forward primer (B3F) (SEQ ID NO:3) and two reverse primers (B3R and B4R) (SEQ ID NOS:4–5) were also designed to recognize highly conserved consensus regions encoding the sequences Gly-Glu-Cys-Val-Cys-Gly-Gln-Cys (SEQ ID NO:58) (B3 region) (SEQ ID NOS:3–4) and Ile-Gly-Leu-Ala-Leu-Leu-Leu-Ile-Trp-Lys (SEQ ID NO:59) (B4 region) (SEQ ID NO:5). The alignment of these primers with previously published sequences of human $\beta_1$, $\beta_2$ and $\beta_3$ and chicken $\beta_1$ is shown in FIG. 1. PCR as described above was performed with cDNA from guinea pig tracheal epithelial cells and the primer pairs BTE2F/B3R (SEQ ID NOS:7 and 4) and B3F/B4R (SEQ ID NOS:3 and 5).

The primer pair BTE2F/B3R (SEQ ID NOS:7 and 4) yielded 1095 additional base pairs of new sequence. Based on this sequence another specific primer (BTE3F) (SEQ ID NO:8) was designed to recognize the sequence Val-Ser-Glu-Asp-Gly-Val (SEQ ID NO:9) near the 3' end of this sequence, and PCR was performed with this primer in combination with primer B4R (SEQ ID NO:5).

FIG. 1 shows the design of the PCR primers. β subunit consensus primer mixtures were designed on the basis of alignment of published sequences of human $\beta_1$, $\beta_2$, $\beta_3$ and chicken $\beta_1$. For forward primers (B1F and B3F) (SEQ ID NOS:1 and 3), the primer sequences included a single nucleotide whenever possible for each of the first two nucleotides of each codon and were usually either degenerate or included deoxyinosine for the third base in codons for amino acids other than methionine. Reverse primers (B2R, B3R, and B4R) (SEQ ID NOS:2, 4 and 5) were designed in the same manner for the complementary DNA strand. Two specific forward primers were designed to recognize $\beta_6$. The first (BTE2F) (SEQ ED NO:7) was designed to work across species and was thus degenerate or included deoxyinosine in the third codon position. The second, BTE3F (SEQ ID NO:8), was not degenerate and was designed to only recognize guinea pig $\beta_6$.

C. Cloning of Fragments Obtained by PCR

Individual fragments were cloned in pBluescript (Stratagene, San Diego, Calif.) as follows. Purified fragments were resuspended in distilled water containing deoxynucleotides and treated with 2.5 units of DNA polymerase I, large fragment (Promega) to fill in any 3' recessed ends left after the last cycle of PCR. The 5' ends were phosphorylated with 5 units of T4 polynucleotide kinase (New England Biolabs, Beverly, Mass.). An aliquot of the above reaction mixture containing approximately 100–200 ng of DNA, was ligated into pBluescript that had been cut with EcoRV (Promega) and dephosphorylated with calf intestinal alkaline phosphatase (Boehringer Mannheim, Indianapolis, Ind.). Ligations were performed at 22° C. for 1 hour with T4 DNA ligase (Bethesda Research Laboratories). The ligation mixture was used to transform competent *Escherichia coli* (JM109, Clontech, San Francisco, Calif.). Plasmids containing inserts were purified using the Pharmacia miniprep lysis kit (Pharmacia LKB Biotechnology, Inc., Piscataway, N.J.) denatured in 0.3 M NaOH, further purified over spin columns containing Sephacryl S-400 (Pharmacia), and then sequenced using the Sequenase™ version 2.0 sequencing kit (United States Biochemical Corp., Cleveland, Ohio) and [$^{35}$S]dATP (Amersham Corp., Arlington Heights, Ill.).

D. Library Screening

PCR fragments generated with the primer pairs B1F/B2R (SEQ ID NOS:1–2) and BTE3F/B4R (SEQ ID NOS:8 and 5) were uniformly labeled with alpha-[$^{32}$P]dCTP and used as probes to screen a random-primed cDNA library and an oligo-dT-primed cDNA library. Both libraries were constructed in the plasmid pTZ18R-BstXI obtained from Invitrogen (San Diego, Calif.) from mRNA obtained from the human pancreatic carcinoma cell line FG-2. Plasmid was purified from clones found to hybridize with either region and inserts were sequenced. A portion of insert DNA from one clone was in turn labeled and used to screen the same libraries. Fourteen independent overlapping clones were sequenced from both ends using primers that recognize regions of the pTZ polylinker. The regions flanking the 3' end of the putative translated region of the new β subunit were sequenced in both directions from three clones using primers constructed to recognize sequences close to the 3' end. On the basis of the initial sequences thus obtained, an additional internal sequence was obtained from clones T10, T11, T12 and T14 (FIG. 2) after digestion with specific restriction endonucleases and relegation. Three internal fragments thus generated were subcloned into pBluescript and were also sequenced in both directions. Approximately 90% of the new sequence reported was obtained from both strands of DNA, and 97% was obtained from two or more overlapping clones (FIG. 2).

FIG. 2 shows a map of the sequencing strategy. Shown are the location of clones used to obtain the partial cDNA sequence of guinea pig $\beta_6$ (clones 1F, 3L, 3N and 3Y, top) and the complete sequence of human $\beta_6$ (clones T1–T19 bottom). Also shown is the location of the translated region (Protein). The location of the transmembrane domain is shown by the letters TM. Clones shown often represent one of several identical clones. Internal sequence of clones with long inserts was obtained by restriction endonuclease digestion and relegation and by ligation of internal fragments into pBluescript. Specific restriction sites employed are shown (Hind, HindIII; Hinc, HincII; Kpn, KpnI; Pst, PstI). The direction and extent of sequencing are shown by arrows. 1109 and 1110 are the sites recognized by oligonucleotide sequencing primers. T18 and T19 each terminated in a poly(A) tail. The regions recognized by the degenerate PCR primers B1F (B1), B2R (B2), B3R/F (B3)., and B4R (B4) and the $\beta_6$ primers BTE2F (BTE2) and BTE3F (BTE3) are noted above the guinea pig cDNA map, kb, kilobases.

E. Nucleotide Sequence of a Novel Guinea Pig Integrin β Subunit

PCR using cDNA from guinea pig airway epithelial cells and the consensus primer mixtures B1F and B2R (FIG. 1) amplified DNA fragments with the expected size of approximately 350 nucleotides. When the fragment DNA was sequenced after cloning into pBluescript, recombinant clones each contained inserts with one of two distinct sequences. One sequence encoded a stretch of 98 amino acids that was 97% identical to the expected region of human $\beta_1$ and was therefore presumed to be guinea pig $B_1$. The other sequence encoded 98 amino acids that were only 53% identical to human $\beta_1$, 45% identical to human $\beta_2$, and 57% identical to human $\beta_3$ (FIG. 2, clone 1F). Both of the guinea pig sequences included the integrin β subunit consensus sequences Ser-X-Ser-Met-X-Asp-Asp-Leu (SEQ ED NO:46) and Gly-Phe-Gly-Ser-Phe-Val (SEQ ID NO:47), and both contained the 2 cysteine residues found in this region in all known integrin β subunits. These data suggest that one of the two sequences we obtained encoded a new member of the integrin β subunit family.

This novel sequence was, extended by further PCR steps utilizing primers specific for the novel sequence (BTE2F, BTE3F) (SEQ ID NOS:7 and 8) in combination with two additional degenerate primers (B3R and B4R, see FIGS. 1, 2 and 4). With the primer pair BTE2F, B3R (SEQ ID NOS:7 and 4) two different cDNA products were obtained (3L and 3N in FIG. 2) due to an unexpected hybridization of the B3R primer with a site 220 nucleotides further downstream (B3' in FIG. 2). The 1732-nucleotide sequence determined from these clones is shown in FIG. 3.

FIG. 3 shows the nucleotide sequences and corresponding amino acid sequences for human (H) $\beta_6$ (SEQ ID NOS:26–27) and guinea pig (GP) $\beta_6$ (SEQ ID NOS:28–29). The amino acid translation is denoted by the single letter code beneath the second nucleotide of each codon from the translated region of human $\beta_6$. For the guinea pig sequence, only amino acids that differ from the human sequence are shown. The numbers along the right-hand margin denote the nucleotide or amino acid number of the last entry on each line. The numbering system used starts with the first nucleotide or amino acid available for each sequence shown. The nine potential sites for N-glycosylation in the putative extracellular domain of human $\beta_6$ are underlined.

F. Nucleotide Sequence of Human $\beta_6$

Screening of cDNA libraries constructed from the human pancreatic carcinoma cell line FG-2 with guinea pig cDNA probes 1F and 3Y (see FIG. 2) and subsequent screening with a probe constructed from a portion of clone T10 (FIG. 2) produced 14 independent positive clones. The two longest clones (T18 and T19) extended to the poly(A) tail. A map of these clones, constructed on the basis of sequence information and of the mobility of inserts cut out of these clones in agarose gels is shown in FIG. 2. This map predicts an mRNA of approximately 5 kilobases including at least a 226-nucleotide untranslated region at the 5' end and, a 2364-nucleotide open reading frame, and a 3' untranslated region of approximately 2.5 kilobases. This molecule has been termed integrin $\beta_6$.

FIG. 3 shows the partial nucleotide and complete amino acid sequences for human $\beta_6$ (SEQ ID NOS:26–27) (excluding most of the 3'-untranslated region) and the alignment of the 1732 nucleotides of sequence obtained from PCR of guinea pig airway epithelial cell cDNA. Of the 577 amino acids deduced from the region sequenced in both species only 36 residues differ; the amino acid sequences are 94% identical. Furthermore, of the 1732 nucleotides sequenced in both species, 91% are identical. Nine potential glycosylation sites present in the putative extracellular domain of human $\beta_6$ are shown by underlining. All seven of these sites that lie within the 577 amino acids obtained for guinea pig $\beta_6$ are also present in the guinea pig protein. If all of the potential glycosylation sites are occupied with oligosaccharides having an average molecular weight of 2,500, the predicted molecular weight of human $\beta_6$ would be 106,000.

Comparison of the 788-amino acid sequence deduced from the open reading frame to the three previously sequenced human β subunits (SEQ ID NOS:30–32) and the myospheroid protein of Drosophila (SEQ ID NO:33) is shown in FIG. 4.

FIG. 4 shows the alignment of $\beta_6$ with four previously reported integrin β subunits. Previously published sequences for human $\beta_1$ (SEQ ID NO:30), human $\beta_2$(SEQ ID NO:31), human $\beta_3$ (SEQ ID NO:32), the myospheroid gene product (βmyo) of Drosophila (SEQ ID NO:33), and the novel sequence described as $\beta_6$ (SEQ ID NO:27) are shown using the single letter amino acid code. The 56 conserved cysteines are noted by * and the 120 other invariant amino acids by=above each line. The transmembrane domain is underlined. The regions used for constructing the consensus β subunit primers B1F (B1) (SEQ ID NO:1), B2R (B2) (SEQ ID NO:2), B3F/R (B3) (SEQ ID NOS:3–4), and B4R (B4) (SEQ ID NO:5) are labeled below the alignment in bold type. The numbers along the right-hand margin denote the number of the last amino acid in each line beginning from the first amino acid of each putative signal sequence.

There are 179 amino acid residues that are identical in each of the other β subunits and in $\beta_6$ including 56 conserved cysteine residues. The overall percentage of identical amino acids between $\beta_6$ and the other human β subunits is 47% for $\beta_3$, 42% for $\beta_1$ and 38% for $\beta_2$. Human $\beta_6$ is also 39% identical to the Drosophila β subunit. Human $\beta_1$, $\beta_2$ and $\beta_3$ and the Drosophila β subunit all have cytoplasmic regions consisting of 41 amino acids (beginning after the putative transmembrane domain shown by the underline in FIG. 4). Although $\beta_6$ contains each of the 10 conserved amino acid residues in this cytoplasmic region it also contains an 11-amino acid extension at the carboxyl terminus. $\beta_6$ also contains two Arg-Gly-Asp sequences, one at amino acids 514–516 and the other at 594–596. These regions could serve as recognition sites for other ligands of the integrin family.

PCR using the primer pair B3F/B4R (SEQ ID NOS:3 and 5) (see FIG. 1) amplified fragments of the expected size of approximately 750 nucleotides. Cloning and sequencing of the fragments did not result in any additional clones containing the novel β subunit sequence but did result in several clones with inserts encoding an amino acid sequence that was 97% identical to the corresponding region of human $\beta_3$ and several others encoding an amino acid sequence that was 93% identical to human $\beta_1$ (SEQ ID NO:35) (FIG. 5). These are presumably the guinea pig homologues of $\beta_1$ (SEQ ID NO:37) and $\beta_3$ (SEQ ID NO:41), respectively. The nucleotide sequences of guinea pig (SEQ ID NO:36) and human $\beta_1$ (SEQ ID NO:34) are 80% identical, and those of guinea pig (SEQ ID NO:40) and human $\beta_3$ (SEQ ID NO:38) are 91% identical.

FIG. 5 shows the alignment of partial nucleotide and amino acid sequences from human (H) and guinea pig (GP) $\beta_1$ (SEQ ID NOS:34–37), $\beta_3$ (SEQ ID NOS:38–41), and $\beta_6$ (SEQ ID NOS:42–45) for the region just downstream from the B3F primer. Amino acid translations denoted by the one-letter code are shown below the second nucleotide of each codon. For the guinea pig sequences, only amino acids that differ from the human sequences are shown. The numbers shown along the right-hand margin denote the nucleotide number for human $\beta_6$. The sequences for human $\beta_1$ and $\beta_3$ are from previously published reports.

EXAMPLE II

$\beta_6$ Associates with $\alpha_V$ and $\alpha_F$ Subunits

To determine that the novel $\beta$ subunit of the present invention is associated with an $\alpha$ chain similar to other known integrins, antisera against peptides from the cytoplasmic domain sequence of $\beta_6$ were prepared. The following amino acid peptides from the cytoplasmic sequence of $\beta_6$ were prepared and used to immunize rabbits: RGSTST-FKNVTYKHR (SEQ ID NO:48) (residues 763–777) and YKHREKQKVDLSTDC (SEQ ID NO:49 (residues 774–788). The antisera were raised in rabbits according to standard procedures known in the art. Briefly, peptides were chemically coupled to keyhole lympet hemocyanin, and were injected in rabbits in either complete (first injection only) or incomplete Freund's adjuvant as described, for example, in Antibodies: A Laboratory Manual, E. Harlow and D. Lowe, eds., Cold Spring Harbor Laboratory, Cold Spring Harbor, N.Y. 11724. Antisera were termed 6830 (to peptides corresponding to residues 763–777) and 6341 (to peptides corresponding to residues 774–788).

The resulting polyclonal antibodies were used to immunoprecipitate detergent lysates from the pancreatic carcinoma cell line FG-2 that had been surface radioiodinated according to procedures well known in the art such as described, for example, in Kajiji et al., EMBO J. 3:673–680 (1989). A complex of two bands was precipitated of respectively 150 kilodaltons (Kd) and 97 Kd in SDS-PAGE under non-reducing conditions. Under reducing conditions, the two bands migrated as a diffused band, extending from 130 Kd to 116 Kd. These bands were specific since pre-immune serum did not precipitate any of them and they were not present when the immunoprecipitation was carried out in the presence of the corresponding immunogenic peptide. Furthermore, the same complex of two bands was precipitated by both the 6830 and 6841 antibodies, which were raised against independent peptides from the cytoplasmic sequence deduced from $\beta_6$ cDNA clones.

To determine which of the two precipitated bands corresponds to $\beta_6$, a SDS-heat denaturated lysate from surface-radioiodinated FG-2 cells was immunoprecipitated with the 6841 antibody. Only the 97 Kd band was detectable (non-reducing conditions), identifying it as the $\beta_6$ band. Under reducing conditions, the apparent molecular weight of this band increased to 116 Kd suggesting the presence of many intra-chain disulfide bonds, which is consistent with the primary structure of $\beta_6$ and of other integrin $\beta$ chains.

The other band, of 150 Kd or 130 Kd under non-reducing or reducing conditions, respectively, is likely to be an $\alpha$ subunit since it dissociates after SDS-heat denaturation of the lysate, indicating that it is non-covalently associated with the $\beta_6$ polypeptide. Furthermore, similar to certain other integrin $\alpha$ chains, its molecular weight decreases under reducing conditions by about 20 Kd (130 Kd versus 150 Kd under non-reducing conditions) probably due to a disulfide linked small peptide that dissociates upon reduction.

To identify which a chain is associated with $\beta_6$, the $\alpha\beta_6$ integrin complex was purified by immuno-affinity chromatography on a 6841-protein A sepharose matrix according to procedures well known in the art such as described, for example, in Kajiji et al., EMBO J. 3:673–680 (1989). The eluted material was immunoprecipitated with antibodies specific for $\alpha_1$, $\alpha_2$, $\alpha_3$, $\alpha_5$, $\alpha_6$ and $\alpha_V$, which are known to be expressed in FG-2 cells. Only the anti-$\alpha_V$ monoclonal antibody 142.19, obtained from Dr. David Cheresh, The Scripps Research Institution, La Jolla, Calif., reacted with the purified material, which indicates that the $\alpha_V$ is associated with $\beta_6$ in this pancreatic carcinoma cell line.

To confirm this data, immunodepletion experiments on surface-radioiodinated FG-2 lysates were performed according to methods well known in the art such as described in Kajiji et al., EMBO J. 3:673–680 (1989). The cell lysate was depleted with the 6841 anti-$\beta_6$ antibody or, in parallel, with a control antiserum, and then immunoprecipitated with the 142.19 anti-$\alpha_V$ antibody. A smaller amount of $\alpha_V$ was present in the immunoprecipitation on the $\beta_6$ depleted lysate and no 97 Kd $\beta_6$ band was visible. Instead, a smaller band of about 90 Kd was present. It is hypothesized that this smaller band represents the $\beta_5$ chain also associated with $\alpha_V$ in these cells. In the control lysate depleted with normal rabbit serum, all three bands, 150 Kd ($\alpha_V$), 97 Kd ($\beta_6$) and 90 Kd ($\beta_5$) were present after immunoprecipitation with the anti-$\alpha_V$ 142.19 antibody.

Another immunodepletion was carried out using 142.19 antibody as the depleting antibody, or in parallel a mouse monoclonal as a control antibody. Immunoprecipitations of $\alpha_V$-depleted lysate with anti-$\alpha_V$ 142.19 antibodies did not show the presence of any band, indicating that all $\alpha_V$-containing integrins had been removed. However, the 6841 anti-$\beta_6$ antibody still precipitated a complex of two bands, one corresponding to $\beta_6$, the other with a molecular weight close to that of $\alpha_V$. This $\alpha$ chain, however, must differ from $\alpha_V$ since it is unreactive with anti-$\alpha_V$ monoclonal antibodies and is referred to herein as $\alpha_F$. In the control depleted lysates, the 6841 anti-$\beta_6$ antibody precipitates much stronger bands, consistent with the possibility that, in FG-2 cells, two $\beta_6$ integrins exist, $\alpha_V\beta_6$ and $\alpha_F\beta_6$.

Although the invention has been described with reference to the presently preferred embodiment, it should be understood that various modifications can be made without departing from the spirit of the invention. Accordingly, the invention is limited only by the claims.

SEQUENCE LISTING (1) GENERAL INFORMATION:

(iii) NUMBER OF SEQUENCES: 62

(2) INFORMATION FOR SEQ ID NO: 1:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

GACMTSTAYT AYYTKATGGA YCT      23

(2) INFORMATION FOR SEQ ID NO: 2:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: modified_base
      (B) LOCATION: 5
      (D) OTHER INFORMATION: /mod_base= OTHER
         /note= "N = deoxyinosine"

(ix) FEATURE:
      (A) NAME/KEY: modified_base
      (B) LOCATION: 14
      (D) OTHER INFORMATION: /mod_base= OTHER
         /note= "N = deoxyinosine"

(ix) FEATURE:
      (A) NAME/KEY: modified_base
      (B) LOCATION: 17
      (D) OTHER INFORMATION: /mod_base= OTHER
         /note= "N = deoxyinosine"

(xi) SEQUENCE DESCRIPTION: SEQ ID NO: 2:

GCATNATKGC RTCNARNCCA CCYTC      25

(2) INFORMATION FOR SEQ ID NO: 3:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: modified_base
      (B) LOCATION: 3
      (D) OTHER INFORMATION: /mod_base= OTHER
         /note= "N = deoxyinosine"

(ix) FEATURE:
      (A) NAME/KEY: modified_base
      (B) LOCATION: 6
      (D) OTHER INFORMATION: /mod_base= OTHER
         /note= "N = deoxyinosine"

-continued

```
    (ix) FEATURE:
         (A) NAME/KEY: modified_base
         (B) LOCATION: 10
         (D) OTHER INFORMATION: /mod_base= OTHER
             /note= "N = deoxyinosine"

(ix) FEATURE:
         (A) NAME/KEY: modified_base
         (B) LOCATION: 18
         (D) OTHER INFORMATION: /mod_base= OTHER
             /note= "N = deoxyinosine"

(xi) SEQUENCE DESCRIPTION: SEQ ID NO: 3:

GGNGANYGTN TTYGTGGNMA GTG                                               23

(2) INFORMATION FOR SEQ ID NO: 4:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: modified_base
         (B) LOCATION: 6
         (D) OTHER INFORMATION: /mod_base= OTHER
             /note= "N = deoxyinosine"

(ix) FEATURE:
         (A) NAME/KEY: modified_base
         (B) LOCATION: 14
         (D) OTHER INFORMATION: /mod_base= OTHER
             /note= "N = deoxyinosine"

(ix) FEATURE:
         (A) NAME/KEY: modified_base
         (B) LOCATION: 18
         (D) OTHER INFORMATION: /mod_base= OTHER
             /note= "N = deoxyinosine"

(xi) SEQUENCE DESCRIPTION: SEQ ID NO: 4:

CACTKNCCAC RAANACRNTC                                                   20

(2) INFORMATION FOR SEQ ID NO: 5:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: DNA (ix) FEATURE:
         (A) NAME/KEY: modified_base
         (B) LOCATION: 6
         (D) OTHER INFORMATION: /mod_base= OTHER
             /note= "N = deoxyinosine"

(ix) FEATURE:
         (A) NAME/KEY: modified_base
         (B) LOCATION: 11
         (D) OTHER INFORMATION: /mod_base= OTHER
             /note= "N = deoxyinosine"

(ix) FEATURE:
         (A) NAME/KEY: modified_base
         (B) LOCATION: 15
         (D) OTHER INFORMATION: /mod_base= OTHER
             /note= "N = deoxyinosine"
```

```
    (ix) FEATURE:
         (A) NAME/KEY: modified_base
         (B) LOCATION: 18
         (D) OTHER INFORMATION: /mod_base= OTHER
             /note= "N = deoxyinosine"

(ix) FEATURE:
         (A) NAME/KEY: modified_base
         (B) LOCATION: 24
         (D) OTHER INFORMATION: /mod_base= OTHER
             /note= "N = deoxyinosine"

(xi) SEQUENCE DESCRIPTION: SEQ ID NO: 5:

TTCCANATSA NYARNRMNRS AAKNCCRAT                                              29

(2) INFORMATION FOR SEQ ID NO: 6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 6:

CCATTGACAA ATGATGCTGA AAGA                                                   24

(2) INFORMATION FOR SEQ ID NO: 7:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (ix) FEATURE:
         (A) NAME/KEY: modified_base
         (B) LOCATION: 3
         (D) OTHER INFORMATION: /mod_base= OTHER
             /note= "N = deoxyinosine"

(ix) FEATURE:
         (A) NAME/KEY: modified_base
         (B) LOCATION: 6
         (D) OTHER INFORMATION: /mod_base= OTHER
             /note= "N = deoxyinosine"

(ix) FEATURE:
         (A) NAME/KEY: modified_base
         (B) LOCATION: 9
         (D) OTHER INFORMATION: /mod_base= OTHER
             /note= "N = deoxyinosine"

(ix) FEATURE:
         (A) NAME/KEY: modified_base
         (B) LOCATION: 18
         (D) OTHER INFORMATION: /mod_base= OTHER
             /note= "N = deoxyinosine"

(xi) SEQUENCE DESCRIPTION: SEQ ID NO: 7:

CCNTTNACNA AYGAYGCNGA AAGA                                                   24

(2) INFORMATION FOR SEQ ID NO: 8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear
```

(ii) MOLECULE TYPE: DNA (xi) SEQUENCE DESCRIPTION: SEQ ID NO: 8:

CATCTCCGAA GACGGCA                                                                17

(2) INFORMATION FOR SEQ ID NO: 9:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ii) MOLECULE TYPE: peptide (xi) SEQUENCE DESCRIPTION: SEQ ID NO: 9:

Val Ser Glu Asp Gly Val
        1               5

(2) INFORMATION FOR SEQ ID NO: 10:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 10:

GACCTGTACT ATCTGATGGA CCT                                                         23

(2) INFORMATION FOR SEQ ID NO: 11:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 11:

GACATCTACT ACTTGATGGA CCT                                                         23

(2) INFORMATION FOR SEQ ID NO: 12:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 12:

GACCTCTACT ACCTTATGGA CCT                                                         23

(2) INFORMATION FOR SEQ ID NO: 13:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO: 13:

GACCTTTATT ATCTTATGGA CCT                                            23

(2) INFORMATION FOR SEQ ID NO: 14:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 14:

GAGGGTGGGC TGGACGCCAT GATGCA                                         26

(2) INFORMATION FOR SEQ ID NO: 15:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 15:

GAGGGTGGCT TTGATGCCAT CATGCA                                         26

(2) INFORMATION FOR SEQ ID NO: 16:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 16:

GAAGGTGGTT TCGATGCCAT CATGCA                                         26

(2) INFORMATION FOR SEQ ID NO: 17:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 17:

GAAGGTGGAT TTGATGCAAT AATGCA                                         26

(2) INFORMATION FOR SEQ ID NO: 18:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (ii) MOLECULE TYPE: DNA (genomic)

(xi) SEQUENCE DESCRIPTION: SEQ ID NO: 18:

GGGGACTGTG TCTGCGGGCA GTGC                                           24

(2) INFORMATION FOR SEQ ID NO: 19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

GGCGAGTGCC TCTGTGGTCA ATGT                        24

(2) INFORMATION FOR SEQ ID NO: 20:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 20:

GGAGAGTGCG TCTGCGGACA GTGT                        24

(2) INFORMATION FOR SEQ ID NO: 21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 21:

GGAGAGTGCA TTTGCGGACA GTGC                        24

(2) INFORMATION FOR SEQ ID NO: 22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 22:

ATCGGCATTC TCCTGCTGGT CATCTGGAAG                  30

(2) INFORMATION FOR SEQ ID NO: 23:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 23:

ATTGGCCTTG CCGCCCTGCT CATCTGGAAA                  30

(2) INFORMATION FOR SEQ ID NO: 24:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 24:

```
ATTGGCCTTG CATTACTGCT GATATGGAAG                                 30
```

(2) INFORMATION FOR SEQ ID NO: 25:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 25:

```
ATTGGACTTG CATTGTTATT GATTTGGAAA                                 30
```

(2) INFORMATION FOR SEQ ID NO: 26:

(i) SEQUENCE CHARACTERISTICS:
        (A) LENGTH: 2644 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 227..2593
        (D) OTHER INFORMATION: /note= "human integrin beta-6 subunit"

(xi) SEQUENCE DESCRIPTION: SEQ ID NO: 26:

```
TAAACACAGC TTTTCTGCTT TACCTGTCCA GGTAGCCTCT GTTTTCATTT CAGTCTTAAT    60

GAAAACTTTC TAACTTATAT CTCAAGTTTC TTTTCAAAGC AGTGTAAGTA GTATTTAAAA   120

TGTTATACTT CAAGAAAGAA AGACTTTAAC GATATTCAGC GTTGGTCTTG TAACGCTGAA   180

GGTAATTCAT TTTTTAATCG GTCTCGCACA GCAAGAACTG AAACGA ATG GGG ATT      235
                                                 Met Gly Ile
                                                  1

GAA CTG CTT TGC CTG TTC TTT CTA TTT CTA GGA AGG AAT GAT TCA CGT    283
Glu Leu Leu Cys Leu Phe Phe Leu Phe Leu Gly Arg Asn Asp Ser Arg
     5                  10                  15

ACA AGG TGG CTG TGC CTG GGA GGT GCA GAA ACC TGT GAA GAC TGC CTG    331
Thr Arg Trp Leu Cys Leu Gly Gly Ala Glu Thr Cys Glu Asp Cys Leu
 20                  25                  30                  35

CTT ATT GGA CCT CAG TGT GCC TGG TGT GCT CAG GAG AAT TTT ACT CAT    379
Leu Ile Gly Pro Gln Cys Ala Trp Cys Ala Gln Glu Asn Phe Thr His
                 40                  45                  50

CCA TCT GGA GTT GGC GAA AGG TGT GAT ACC CCA GCA AAC CTT TTA GCT    427
Pro Ser Gly Val Gly Glu Arg Cys Asp Thr Pro Ala Asn Leu Leu Ala
             55                  60                  65

AAA GGA TGT CAA TTA AAC TTC ATC GAA AAC CCT GTC TCC CAA GTA GAA    475
Lys Gly Cys Gln Leu Asn Phe Ile Glu Asn Pro Val Ser Gln Val Glu
     70                  75                  80
```

```
ATA CTT AAA AAT AAG CCT CTC AGT GTA GGC AGA CAG AAA AAT AGT TCT      523
Ile Leu Lys Asn Lys Pro Leu Ser Val Gly Arg Gln Lys Asn Ser Ser
    85              90                  95

GAC ATT GTT CAG ATT GCA CCT CAA AGC TTG ATC CTT AAG TTG AGA CCA      571
Asp Ile Val Gln Ile Ala Pro Gln Ser Leu Ile Leu Lys Leu Arg Pro
100             105                 110                 115

GGT GGT GCG CAG ACT CTG CAG GTG CAT GTC CGC CAG ACT GAG GAC TAC      619
Gly Gly Ala Gln Thr Leu Gln Val His Val Arg Gln Thr Glu Asp Tyr
                120                 125                 130

CCG GTG GAT TTG TAT TAC CTC ATG GAC CTC TCC GCC TCC ATG GAT GAC      667
Pro Val Asp Leu Tyr Tyr Leu Met Asp Leu Ser Ala Ser Met Asp Asp
            135                 140                 145

GAC CTC AAC ACA ATA AAG GAG CTG GGC TCC GGC CTT TCC AAA GAG ATG      715
Asp Leu Asn Thr Ile Lys Glu Leu Gly Ser Gly Leu Ser Lys Glu Met
        150                 155                 160

TCT AAA TTA ACC AGC AAC TTT AGA CTG GGC TTC GGA TCT TTT GTG GAA      763
Ser Lys Leu Thr Ser Asn Phe Arg Leu Gly Phe Gly Ser Phe Val Glu
    165                 170                 175

AAA CCT GTA TCC CCT TTT GTG AAA ACA ACA CCA GAA GAA ATT GCC AAC      811
Lys Pro Val Ser Pro Phe Val Lys Thr Thr Pro Glu Glu Ile Ala Asn
180             185                 190                 195

CCT TGC AGT AGT ATT CCA TAC TTC TGT TTA CCT ACA TTT GGA TTC AAG      859
Pro Cys Ser Ser Ile Pro Tyr Phe Cys Leu Pro Thr Phe Gly Phe Lys
                200                 205                 210

CAC ATT TTG CCA TTG ACA AAT GAT GCT GAA AGA TTC AAT GAA ATT GTG      907
His Ile Leu Pro Leu Thr Asn Asp Ala Glu Arg Phe Asn Glu Ile Val
            215                 220                 225

AAG AAT CAG AAA ATT TCT GCT AAT ATT GAC ACA CCC GAA GGT GGA TTT      955
Lys Asn Gln Lys Ile Ser Ala Asn Ile Asp Thr Pro Glu Gly Gly Phe
        230                 235                 240

GAT GCA ATT ATG CAA GCT GCT GTG TGT AAG GAA AAA ATT GGC TGG CGG     1003
Asp Ala Ile Met Gln Ala Ala Val Cys Lys Glu Lys Ile Gly Trp Arg
    245                 250                 255

AAT GAC TCC CTC CAC CTC CTG GTC TTT GTG AGT GAT GCT GAT TCT CAT     1051
Asn Asp Ser Leu His Leu Leu Val Phe Val Ser Asp Ala Asp Ser His
260             265                 270                 275

TTT GGA ATG GAC AGC AAA CTA GCA GGC ATC GTC ATT CCT AAT GAC GGG     1099
Phe Gly Met Asp Ser Lys Leu Ala Gly Ile Val Ile Pro Asn Asp Gly
                280                 285                 290

CTC TGT CAC TTG GAC AGC AAG AAT GAA TAC TCC ATG TCA ACT GTC TTG     1147
Leu Cys His Leu Asp Ser Lys Asn Glu Tyr Ser Met Ser Thr Val Leu
            295                 300                 305

GAA TAT CCA ACA ATT GGA CAA CTC ATT GAT AAA CTG GTA CAA AAC AAC     1195
Glu Tyr Pro Thr Ile Gly Gln Leu Ile Asp Lys Leu Val Gln Asn Asn
        310                 315                 320

GTG TTA TTG ATC TTC GCT GTA ACC CAA GAA CAA GTT CAT TTA TAT GAG     1243
Val Leu Leu Ile Phe Ala Val Thr Gln Glu Gln Val His Leu Tyr Glu
    325                 330                 335

AAT TAC GCA AAA CTT ATT CCT GGA GCT ACA GTA GGT CTA CTT CAG AAG     1291
Asn Tyr Ala Lys Leu Ile Pro Gly Ala Thr Val Gly Leu Leu Gln Lys
340             345                 350                 355

GAC TCC GGA AAC ATT CTC CAG CTG ATC ATC TCA GCT TAT GAA GAA CTG     1339
Asp Ser Gly Asn Ile Leu Gln Leu Ile Ile Ser Ala Tyr Glu Glu Leu
                360                 365                 370

CGG TCT GAG GTG GAA CTG GAA GTA TTA GGA GAC ACT GAA GGA CTC AAC     1387
Arg Ser Glu Val Glu Leu Glu Val Leu Gly Asp Thr Glu Gly Leu Asn
            375                 380                 385

TTG TCA TTT ACA GCC ATC TGT AAC AAC GGT ACC CTC TTC CAA CAC CAA     1435
Leu Ser Phe Thr Ala Ile Cys Asn Asn Gly Thr Leu Phe Gln His Gln
        390                 395                 400
```

-continued

| | |
|---|---|
| AAG AAA TGC TCT CAC ATG AAA GTG GGA GAC ACA GCT TCC TTC AGC GTG<br>Lys Lys Cys Ser His Met Lys Val Gly Asp Thr Ala Ser Phe Ser Val<br>405                                    410                         415 | 1483 |
| ACT GTG AAT ATC CCA CAC TGC GAG AGA AGA AGC AGG CAC ATT ATC ATA<br>Thr Val Asn Ile Pro His Cys Glu Arg Arg Ser Arg His Ile Ile Ile<br>420                             425                         430                     435 | 1531 |
| AAG CCT GTG GGG CTG GGG GAT GCC CTG GAA TTA CTT GTC AGC CCA GAA<br>Lys Pro Val Gly Leu Gly Asp Ala Leu Glu Leu Leu Val Ser Pro Glu<br>                    440                         445                         450 | 1579 |
| TGC AAC TGC GAC TGT CAG AAA GAA GTG GAA GTG AAC AGC TCC AAA TGT<br>Cys Asn Cys Asp Cys Gln Lys Glu Val Glu Val Asn Ser Ser Lys Cys<br>                    455                         460                         465 | 1627 |
| CAC CAC GGG AAC GGC TCT TTC CAG TGT GGG GTG TGT GCC TGC CAC CCT<br>His His Gly Asn Gly Ser Phe Gln Cys Gly Val Cys Ala Cys His Pro<br>                    470                         475                         480 | 1675 |
| GGC CAC ATG GGG CCT CGC TGT GAG TGT GGC GAG GAC ATG CTG AGC ACA<br>Gly His Met Gly Pro Arg Cys Glu Cys Gly Glu Asp Met Leu Ser Thr<br>                    485                         490                         495 | 1723 |
| GAT TCC TGC AAG GAG GCC CCA GAT CAT CCC TCC TGC AGC GGA AGG GGT<br>Asp Ser Cys Lys Glu Ala Pro Asp His Pro Ser Cys Ser Gly Arg Gly<br>500                                    505                         510                     515 | 1771 |
| GAC TGC TAC TGT GGG CAG TGT ATC TGC CAC TTG TCT CCC TAT GGA AAC<br>Asp Cys Tyr Cys Gly Gln Cys Ile Cys His Leu Ser Pro Tyr Gly Asn<br>                    520                         525                         530 | 1819 |
| ATT TAT GGA CCT TAT TGC CAG TGT GAC AAT TTC TCC TGC GTG AGA CAC<br>Ile Tyr Gly Pro Tyr Cys Gln Cys Asp Asn Phe Ser Cys Val Arg His<br>                    535                         540                         545 | 1867 |
| AAA GGG CTG CTC TGC GGA GGT AAC GGC GAC TGT GAC TGT GGT GAA TGT<br>Lys Gly Leu Leu Cys Gly Gly Asn Gly Asp Cys Asp Cys Gly Glu Cys<br>                    550                         555                         560 | 1915 |
| GTG TGC AGG AGC GGC TGG ACT GGC GAG TAC TGC AAC TGC ACC ACC AGC<br>Val Cys Arg Ser Gly Trp Thr Gly Glu Tyr Cys Asn Cys Thr Thr Ser<br>565                                    570                         575 | 1963 |
| ACG GAC TCC TGC GTC TCT GAA GAT GGA GTG CTC TGC AGC GGG CGC GGG<br>Thr Asp Ser Cys Val Ser Glu Asp Gly Val Leu Cys Ser Gly Arg Gly<br>580                                    585                         590                     595 | 2011 |
| GAC TGT GTT TGT GGC AAG TGT GTT TGC ACA AAC CCT GGA GCC TCA GGA<br>Asp Cys Val Cys Gly Lys Cys Val Cys Thr Asn Pro Gly Ala Ser Gly<br>                    600                         605                         610 | 2059 |
| CCA ACC TGT GAA CGA TGT CCT ACC TGT GGT GAC CCC TGT AAC TCT AAA<br>Pro Thr Cys Glu Arg Cys Pro Thr Cys Gly Asp Pro Cys Asn Ser Lys<br>                    615                         620                         625 | 2107 |
| CGG AGC TGC ATT GAG TGC CAC CTG TCA GCA GCT GGC CAA GCC GGA GAA<br>Arg Ser Cys Ile Glu Cys His Leu Ser Ala Ala Gly Gln Ala Gly Glu<br>                    630                         635                         640 | 2155 |
| GAA TGT GTG GAC AAG TGC AAA CTA GCT GGT GCG ACC ATC AGT GAA GAA<br>Glu Cys Val Asp Lys Cys Lys Leu Ala Gly Ala Thr Ile Ser Glu Glu<br>645                                    650                         655 | 2203 |
| GAA GAT TTC TCA AAG GAT GGT TCT GTT TCC TGC TCT CTG CAA GGA GAA<br>Glu Asp Phe Ser Lys Asp Gly Ser Val Ser Cys Ser Leu Gln Gly Glu<br>660                                    665                         670                     675 | 2251 |
| AAT GAA TGT TTA ATT ACA TTC TTA ATA ACT ACA GAT AAT GAG GGG AAA<br>Asn Glu Cys Leu Ile Thr Phe Leu Ile Thr Thr Asp Asn Glu Gly Lys<br>                    680                         685                         690 | 2299 |
| ACC ATC ATT CAC AGC ATC AAT GAA AAA GAT TGT CCG AAG CCT CCA AAC<br>Thr Ile Ile His Ser Ile Asn Glu Lys Asp Cys Pro Lys Pro Pro Asn<br>                    695                         700                         705 | 2347 |
| ATT CCC ATG ATC ATG TTA GGG GTT TCC CTG GCT ACT CTT CTC ATC GGG<br>Ile Pro Met Ile Met Leu Gly Val Ser Leu Ala Thr Leu Leu Ile Gly<br>                    710                         715                     720 | 2395 |

```
GTT GTC CTA CTG TGC ATC TGG AAG CTA CTG GTG TCA TTT CAT GAT CGT      2443
Val Val Leu Leu Cys Ile Trp Lys Leu Leu Val Ser Phe His Asp Arg
725                 730                 735

AAA GAA GTT GCC AAA TTT GAA GCA GAA CGA TCA AAA GCC AAG TGG CAA      2491
Lys Glu Val Ala Lys Phe Glu Ala Glu Arg Ser Lys Ala Lys Trp Gln
740                 745                 750                 755

ACG GGA ACC AAT CCA CTC TAC AGA GGA TCC ACA AGT ACT TTT AAA AAT      2539
Thr Gly Thr Asn Pro Leu Tyr Arg Gly Ser Thr Ser Thr Phe Lys Asn
                760                 765                 770

GTA ACT TAT AAA CAC AGG GAA AAA CAA AAG GTA GAC CTT TCC ACA GAT      2587
Val Thr Tyr Lys His Arg Glu Lys Gln Lys Val Asp Leu Ser Thr Asp
            775                 780                 785

TGC TAGAACTACT TTATGCATAA AAAAAGTCTG TTTCACTGAT ATGAAATGTT AATG      2644
Cys
```

(2) INFORMATION FOR SEQ ID NO: 27:

(i) SEQUENCE CHARACTERISTICS:
        (A) LENGTH: 788 amino acids
        (B) TYPE: amino acid
        (D) TOPOLOGY: linear (ii) MOLECULE TYPE: protein (xi) SEQUENCE DESCRIPTION: SEQ ID NO: 27:

```
Met Gly Ile Glu Leu Leu Cys Leu Phe Phe Leu Phe Leu Gly Arg Asn
1               5                   10                  15

Asp Ser Arg Thr Arg Trp Leu Cys Leu Gly Gly Ala Glu Thr Cys Glu
            20                  25                  30

Asp Cys Leu Leu Ile Gly Pro Gln Cys Ala Trp Cys Ala Gln Glu Asn
        35                  40                  45

Phe Thr His Pro Ser Gly Val Gly Glu Arg Cys Asp Thr Pro Ala Asn
    50                  55                  60

Leu Leu Ala Lys Gly Cys Gln Leu Asn Phe Ile Glu Asn Pro Val Ser
65                  70                  75                  80

Gln Val Glu Ile Leu Lys Asn Lys Pro Leu Ser Val Gly Arg Gln Lys
                85                  90                  95

Asn Ser Ser Asp Ile Val Gln Ile Ala Pro Gln Ser Leu Ile Leu Lys
            100                 105                 110

Leu Arg Pro Gly Gly Ala Gln Thr Leu Gln Val His Val Arg Gln Thr
        115                 120                 125

Glu Asp Tyr Pro Val Asp Leu Tyr Tyr Leu Met Asp Leu Ser Ala Ser
    130                 135                 140

Met Asp Asp Asp Leu Asn Thr Ile Lys Glu Leu Gly Ser Gly Leu Ser
145                 150                 155                 160

Lys Glu Met Ser Lys Leu Thr Ser Asn Phe Arg Leu Gly Phe Gly Ser
                165                 170                 175

Phe Val Glu Lys Pro Val Ser Pro Phe Val Lys Thr Thr Pro Glu Glu
            180                 185                 190

Ile Ala Asn Pro Cys Ser Ser Ile Pro Tyr Phe Cys Leu Pro Thr Phe
        195                 200                 205

Gly Phe Lys His Ile Leu Pro Leu Thr Asn Asp Ala Glu Arg Phe Asn
    210                 215                 220

Glu Ile Val Lys Asn Gln Lys Ile Ser Ala Asn Ile Asp Thr Pro Glu
225                 230                 235                 240

Gly Gly Phe Asp Ala Ile Met Gln Ala Ala Val Cys Lys Glu Lys Ile
                245                 250                 255
```

-continued

```
Gly Trp Arg Asn Asp Ser Leu His Leu Leu Val Phe Val Ser Asp Ala
                260                 265                 270

Asp Ser His Phe Gly Met Asp Ser Lys Leu Ala Gly Ile Val Ile Pro
            275                 280                 285

Asn Asp Gly Leu Cys His Leu Asp Ser Lys Asn Glu Tyr Ser Met Ser
        290                 295                 300

Thr Val Leu Glu Tyr Pro Thr Ile Gly Gln Leu Ile Asp Lys Leu Val
305                 310                 315                 320

Gln Asn Asn Val Leu Leu Ile Phe Ala Val Thr Gln Glu Gln Val His
                325                 330                 335

Leu Tyr Glu Asn Tyr Ala Lys Leu Ile Pro Gly Ala Thr Val Gly Leu
            340                 345                 350

Leu Gln Lys Asp Ser Gly Asn Ile Leu Gln Leu Ile Ile Ser Ala Tyr
        355                 360                 365

Glu Glu Leu Arg Ser Glu Val Glu Leu Glu Val Leu Gly Asp Thr Glu
370                 375                 380

Gly Leu Asn Leu Ser Phe Thr Ala Ile Cys Asn Asn Gly Thr Leu Phe
385                 390                 395                 400

Gln His Gln Lys Lys Cys Ser His Met Lys Val Gly Asp Thr Ala Ser
                405                 410                 415

Phe Ser Val Thr Val Asn Ile Pro His Cys Glu Arg Arg Ser Arg His
            420                 425                 430

Ile Ile Ile Lys Pro Val Gly Leu Gly Asp Ala Leu Glu Leu Leu Val
        435                 440                 445

Ser Pro Glu Cys Asn Cys Asp Cys Gln Lys Glu Val Glu Val Asn Ser
450                 455                 460

Ser Lys Cys His His Gly Asn Gly Ser Phe Gln Cys Gly Val Cys Ala
465                 470                 475                 480

Cys His Pro Gly His Met Gly Pro Arg Cys Glu Cys Gly Glu Asp Met
                485                 490                 495

Leu Ser Thr Asp Ser Cys Lys Glu Ala Pro Asp His Pro Ser Cys Ser
            500                 505                 510

Gly Arg Gly Asp Cys Tyr Cys Gly Gln Cys Ile Cys His Leu Ser Pro
        515                 520                 525

Tyr Gly Asn Ile Tyr Gly Pro Tyr Cys Gln Cys Asp Asn Phe Ser Cys
        530                 535                 540

Val Arg His Lys Gly Leu Leu Cys Gly Gly Asn Gly Asp Cys Asp Cys
545                 550                 555                 560

Gly Glu Cys Val Cys Arg Ser Gly Trp Thr Gly Glu Tyr Cys Asn Cys
                565                 570                 575

Thr Thr Ser Thr Asp Ser Cys Val Ser Glu Asp Gly Val Leu Cys Ser
            580                 585                 590

Gly Arg Gly Asp Cys Val Cys Gly Lys Cys Val Cys Thr Asn Pro Gly
        595                 600                 605

Ala Ser Gly Pro Thr Cys Glu Arg Cys Pro Thr Cys Gly Asp Pro Cys
610                 615                 620

Asn Ser Lys Arg Ser Cys Ile Glu Cys His Leu Ser Ala Ala Gly Gln
625                 630                 635                 640

Ala Gly Glu Glu Cys Val Asp Lys Cys Lys Leu Ala Gly Ala Thr Ile
                645                 650                 655

Ser Glu Glu Glu Asp Phe Ser Lys Asp Gly Ser Val Ser Cys Ser Leu
            660                 665                 670
```

-continued

```
Gln Gly Glu Asn Glu Cys Leu Ile Thr Phe Leu Ile Thr Thr Asp Asn
        675                 680                 685

Glu Gly Lys Thr Ile Ile His Ser Ile Asn Glu Lys Asp Cys Pro Lys
        690                 695                 700

Pro Pro Asn Ile Pro Met Ile Met Leu Gly Val Ser Leu Ala Thr Leu
705                 710                 715                 720

Leu Ile Gly Val Val Leu Leu Cys Ile Trp Lys Leu Leu Val Ser Phe
                725                 730                 735

His Asp Arg Lys Glu Val Ala Lys Phe Glu Ala Glu Arg Ser Lys Ala
        740                 745                 750

Lys Trp Gln Thr Gly Thr Asn Pro Leu Tyr Arg Gly Ser Thr Ser Thr
        755                 760                 765

Phe Lys Asn Val Thr Tyr Lys His Arg Glu Lys Gln Lys Val Asp Leu
770                 775                 780

Ser Thr Asp Cys
785
```

(2) INFORMATION FOR SEQ ID NO: 28:

(i) SEQUENCE CHARACTERISTICS:
        (A) LENGTH: 1732 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1731
        (D) OTHER INFORMATION: /note= "partial guinea pig integrin
            beta-6 subunit"

(xi) SEQUENCE DESCRIPTION: SEQ ID NO: 28:

```
TCC GCC TCC ATG GAC GAT GAC CTC AAC ACA ATC AAA GAG CTG GGC TCC        48
Ser Ala Ser Met Asp Asp Asp Leu Asn Thr Ile Lys Glu Leu Gly Ser
  1               5                  10                  15

CTG CTT TCA AAG GAG ATG TCT AAA TTA ACT AGC AAC TTT AGA CTG GGC        96
Leu Leu Ser Lys Glu Met Ser Lys Leu Thr Ser Asn Phe Arg Leu Gly
             20                  25                  30

TTC GGC TCT TTT GTA GAA AAA CCC GTC TCC CCT TTT ATG AAA ACA ACA       144
Phe Gly Ser Phe Val Glu Lys Pro Val Ser Pro Phe Met Lys Thr Thr
         35                  40                  45

CCA GAG GAA ATT GCC AAC CCT TGC AGT AGT ATT CCA TAT ATC TGC TTA       192
Pro Glu Glu Ile Ala Asn Pro Cys Ser Ser Ile Pro Tyr Ile Cys Leu
 50                  55                  60

CCT ACA TTT GGA TTC AAG CAC ATT CTG CCA TTG ACA AAT GAT GCT GAA       240
Pro Thr Phe Gly Phe Lys His Ile Leu Pro Leu Thr Asn Asp Ala Glu
 65                  70                  75                  80

AGA TTC AAT GAA ATT GTG AAG AAA CAG AAA ATT TCT GCT AAT ATT GAC       288
Arg Phe Asn Glu Ile Val Lys Lys Gln Lys Ile Ser Ala Asn Ile Asp
                 85                  90                  95

AAC CCT GAA GGT GGA TTC GAC GCC ATT ATG CAA GCT GCT GTG TGT AAG       336
Asn Pro Glu Gly Gly Phe Asp Ala Ile Met Gln Ala Ala Val Cys Lys
            100                 105                 110

GAA AAA ATT GGC TGG CGG AAT GAT TCG CTC CAT CTC CTA GTC TTC GTG       384
Glu Lys Ile Gly Trp Arg Asn Asp Ser Leu His Leu Leu Val Phe Val
        115                 120                 125

AGT GAT GCC GAT TCT CAT TTT GGA ATG GAC AGC AAA CTG GCA GGC ATT       432
Ser Asp Ala Asp Ser His Phe Gly Met Asp Ser Lys Leu Ala Gly Ile
    130                 135                 140
```

```
                                                    -continued

GTC ATT CCC AAC GAT GGG CTG TGT CAC TTG GAC AGC AAG AAT GAA TAC    480
Val Ile Pro Asn Asp Gly Leu Cys His Leu Asp Ser Lys Asn Glu Tyr
145             150                 155                 160

TCC ATG TCA ACT GTC ATG GAA TAT CCA ACA ATT GGA CAA CTC ATT GAT    528
Ser Met Ser Thr Val Met Glu Tyr Pro Thr Ile Gly Gln Leu Ile Asp
                165                 170                 175

AAA GTG GTA CAA AAC AAT GTG TTA CTG ATC TTT GCT GTA ACC CAA GAA    576
Lys Val Val Gln Asn Asn Val Leu Leu Ile Phe Ala Val Thr Gln Glu
            180                 185                 190

CAA GTT CCA CTA TAT GAG AAT TAT GCA AAA CTT ATT CCT GGA GCC ACA    624
Gln Val Pro Leu Tyr Glu Asn Tyr Ala Lys Leu Ile Pro Gly Ala Thr
        195                 200                 205

GTG GGG CTA CTT CAC AAG GAC TCT GGA AAC ATT CTC CAA CTG ATC ATC    672
Val Gly Leu Leu His Lys Asp Ser Gly Asn Ile Leu Gln Leu Ile Ile
210                 215                 220

TCA GCT TAT GAA GAA CTG CGG TCT GAG GTG GAG CTG GAA GTA TTA GGA    720
Ser Ala Tyr Glu Glu Leu Arg Ser Glu Val Glu Leu Glu Val Leu Gly
225                 230                 235                 240

GAT ACA GAG GGC CTC AAT CTT TCG TTC TCA GCT GTC TGT AAC AAT GGC    768
Asp Thr Glu Gly Leu Asn Leu Ser Phe Ser Ala Val Cys Asn Asn Gly
                245                 250                 255

ACT CTC TTC CCA CAC CAA AAG AAA TGC TTG CAC ATG AAA GTG GGA GAA    816
Thr Leu Phe Pro His Gln Lys Lys Cys Leu His Met Lys Val Gly Glu
            260                 265                 270

ACA GCT TCA TTC AAT GTG ACT GTG AGT ATA CCA AAC TGT GAG AGA AAA    864
Thr Ala Ser Phe Asn Val Thr Val Ser Ile Pro Asn Cys Glu Arg Lys
        275                 280                 285

AGC AGG CAT GTT ATC ATA AAG CCT GTG GGG CTG GGG GAC ACC CTG GAA    912
Ser Arg His Val Ile Ile Lys Pro Val Gly Leu Gly Asp Thr Leu Glu
290                 295                 300

ATC CTT GTC AGC CCA GAA TGC AGC TGC GAT TGT CAG AAA GAA GTG GAA    960
Ile Leu Val Ser Pro Glu Cys Ser Cys Asp Cys Gln Lys Glu Val Glu
305                 310                 315                 320

GTG AAC AGC TCC AAA TGC CAC AAT GGG AAC GGC TCC TAC CAG TGT GGG   1008
Val Asn Ser Ser Lys Cys His Asn Gly Asn Gly Ser Tyr Gln Cys Gly
                325                 330                 335

GTG TGT GCC TGT AAC CCA GGC CAC ATG GGC CCT CAC TGC GAG TGT GGT   1056
Val Cys Ala Cys Asn Pro Gly His Met Gly Pro His Cys Glu Cys Gly
            340                 345                 350

GAG GAC ACG CTG AGC ACA GAT TCC TGC AAG GAG ACC CCA GAC CAT CCC   1104
Glu Asp Thr Leu Ser Thr Asp Ser Cys Lys Glu Thr Pro Asp His Pro
        355                 360                 365

TCG TGC AGC GGA AGG GGT GAC TGC TAC TGT GGG CAG TGC ATC TGC CAC   1152
Ser Cys Ser Gly Arg Gly Asp Cys Tyr Cys Gly Gln Cys Ile Cys His
370                 375                 380

TTG TCT CCC TAT GGA AAC ATT TAT GGA CCT TAC TGC CAG TGT GAC AAT   1200
Leu Ser Pro Tyr Gly Asn Ile Tyr Gly Pro Tyr Cys Gln Cys Asp Asn
385                 390                 395                 400

TTC TCC TGT GTG AGG CAC AAA GGG CTG CTC TGT GGA GAT AAC GGA GAC   1248
Phe Ser Cys Val Arg His Lys Gly Leu Leu Cys Gly Asp Asn Gly Asp
                405                 410                 415

TGT GAA TGT GGG GAA TGC GTG TGC AGG AGT GGT TGG ACC GGA GAG TAC   1296
Cys Glu Cys Gly Glu Cys Val Cys Arg Ser Gly Trp Thr Gly Glu Tyr
            420                 425                 430

TGC AAC TGT ACC ACC AGC ACA GAC ACC TGC ATC TCC GAA GAC GGC ACG   1344
Cys Asn Cys Thr Thr Ser Thr Asp Thr Cys Ile Ser Glu Asp Gly Thr
        435                 440                 445

CTC TGC AGC GGG CGC GGG GAC TGC GTC TGT GGC AAG TGT GTC TGC ACG   1392
Leu Cys Ser Gly Arg Gly Asp Cys Val Cys Gly Lys Cys Val Cys Thr
450                 455                 460
```

```
AAC CCT GGA GCC TCG GGA CCC ACC TGT GAA CGA TGT CCT ACC TGT AGT    1440
Asn Pro Gly Ala Ser Gly Pro Thr Cys Glu Arg Cys Pro Thr Cys Ser
465             470                 475                 480

GAC CCC TGT AAC TCT AAA CGG AGC TGC ATT GAA TGC CAC CTG TCT GCA    1488
Asp Pro Cys Asn Ser Lys Arg Ser Cys Ile Glu Cys His Leu Ser Ala
                485                 490                 495

GAT GGT CAG CCT GGA GAA GAA TGT GTG GAC AAA TGC AAA CTA GCA GGT    1536
Asp Gly Gln Pro Gly Glu Glu Cys Val Asp Lys Cys Lys Leu Ala Gly
            500                 505                 510

GTG ACC ATC AGC AAA GAA GCA GAT TTC TCA AAG GAT AGT TCT GTT TCC    1584
Val Thr Ile Ser Lys Glu Ala Asp Phe Ser Lys Asp Ser Ser Val Ser
        515                 520                 525

TGC TCC CTG CAA GGA GAA AAT GAA TGT CTT ATT ACA TTC CTA ATA AGT    1632
Cys Ser Leu Gln Gly Glu Asn Glu Cys Leu Ile Thr Phe Leu Ile Ser
    530                 535                 540

ACA GAT AAT GAG GGA AAA ACC ATC ATT CAC AAC ATC AGT GAA AAA GAC    1680
Thr Asp Asn Glu Gly Lys Thr Ile Ile His Asn Ile Ser Glu Lys Asp
545                 550                 555                 560

TGC CCC AAA CCT CCA AAT ATT CCT ATG ATC ATG TTG GGG GTT TCA CTG    1728
Cys Pro Lys Pro Pro Asn Ile Pro Met Ile Met Leu Gly Val Ser Leu
                565                 570                 575

GCT A                                                              1732
Ala
```

(2) INFORMATION FOR SEQ ID NO: 29:

(i) SEQUENCE CHARACTERISTICS:
        (A) LENGTH: 577 amino acids
        (B) TYPE: amino acid
        (D) TOPOLOGY: linear (ii) MOLECULE TYPE: protein (xi) SEQUENCE DESCRIPTION: SEQ ID NO: 29:

```
Ser Ala Ser Met Asp Asp Leu Asn Thr Ile Lys Glu Leu Gly Ser
1               5                   10                  15

Leu Leu Ser Lys Glu Met Ser Lys Leu Thr Ser Asn Phe Arg Leu Gly
            20                  25                  30

Phe Gly Ser Phe Val Glu Lys Pro Val Ser Pro Phe Met Lys Thr Thr
        35                  40                  45

Pro Glu Glu Ile Ala Asn Pro Cys Ser Ser Ile Pro Tyr Ile Cys Leu
    50                  55                  60

Pro Thr Phe Gly Phe Lys His Ile Leu Pro Leu Thr Asn Asp Ala Glu
65                  70                  75                  80

Arg Phe Asn Glu Ile Val Lys Lys Gln Lys Ile Ser Ala Asn Ile Asp
                85                  90                  95

Asn Pro Glu Gly Gly Phe Asp Ala Ile Met Gln Ala Ala Val Cys Lys
            100                 105                 110

Glu Lys Ile Gly Trp Arg Asn Asp Ser Leu His Leu Leu Val Phe Val
        115                 120                 125

Ser Asp Ala Asp Ser His Phe Gly Met Asp Ser Lys Leu Ala Gly Ile
    130                 135                 140

Val Ile Pro Asn Asp Gly Leu Cys His Leu Asp Ser Lys Asn Glu Tyr
145                 150                 155                 160

Ser Met Ser Thr Val Met Glu Tyr Pro Thr Ile Gly Gln Leu Ile Asp
                165                 170                 175

Lys Val Val Gln Asn Asn Val Leu Leu Ile Phe Ala Val Thr Gln Glu
            180                 185                 190
```

```
Gln Val Pro Leu Tyr Glu Asn Tyr Ala Lys Leu Ile Pro Gly Ala Thr
            195                 200                 205

Val Gly Leu Leu His Lys Asp Ser Gly Asn Ile Leu Gln Leu Ile Ile
    210                 215                 220

Ser Ala Tyr Glu Glu Leu Arg Ser Glu Val Glu Leu Glu Val Leu Gly
225                 230                 235                 240

Asp Thr Glu Gly Leu Asn Leu Ser Phe Ser Ala Val Cys Asn Asn Gly
                245                 250                 255

Thr Leu Phe Pro His Gln Lys Lys Cys Leu His Met Lys Val Gly Glu
            260                 265                 270

Thr Ala Ser Phe Asn Val Thr Val Ser Ile Pro Asn Cys Glu Arg Lys
        275                 280                 285

Ser Arg His Val Ile Ile Lys Pro Val Gly Leu Gly Asp Thr Leu Glu
    290                 295                 300

Ile Leu Val Ser Pro Glu Cys Ser Cys Asp Cys Gln Lys Glu Val Glu
305                 310                 315                 320

Val Asn Ser Ser Lys Cys His Asn Gly Asn Gly Ser Tyr Gln Cys Gly
                325                 330                 335

Val Cys Ala Cys Asn Pro Gly His Met Gly Pro His Cys Glu Cys Gly
            340                 345                 350

Glu Asp Thr Leu Ser Thr Asp Ser Cys Lys Glu Thr Pro Asp His Pro
        355                 360                 365

Ser Cys Ser Gly Arg Gly Asp Cys Tyr Cys Gly Gln Cys Ile Cys His
    370                 375                 380

Leu Ser Pro Tyr Gly Asn Ile Tyr Gly Pro Tyr Cys Gln Cys Asp Asn
385                 390                 395                 400

Phe Ser Cys Val Arg His Lys Gly Leu Leu Cys Gly Asp Asn Gly Asp
                405                 410                 415

Cys Glu Cys Gly Glu Cys Val Cys Arg Ser Gly Trp Thr Gly Glu Tyr
            420                 425                 430

Cys Asn Cys Thr Thr Ser Thr Asp Thr Cys Ile Ser Glu Asp Gly Thr
        435                 440                 445

Leu Cys Ser Gly Arg Gly Asp Cys Val Cys Gly Lys Cys Val Cys Thr
    450                 455                 460

Asn Pro Gly Ala Ser Gly Pro Thr Cys Glu Arg Cys Pro Thr Cys Ser
465                 470                 475                 480

Asp Pro Cys Asn Ser Lys Arg Ser Cys Ile Glu Cys His Leu Ser Ala
                485                 490                 495

Asp Gly Gln Pro Gly Glu Glu Cys Val Asp Lys Cys Lys Leu Ala Gly
            500                 505                 510

Val Thr Ile Ser Lys Glu Ala Asp Phe Ser Lys Asp Ser Ser Val Ser
        515                 520                 525

Cys Ser Leu Gln Gly Glu Asn Glu Cys Leu Ile Thr Phe Leu Ile Ser
    530                 535                 540

Thr Asp Asn Glu Gly Lys Thr Ile Ile His Asn Ile Ser Glu Lys Asp
545                 550                 555                 560

Cys Pro Lys Pro Pro Asn Ile Pro Met Ile Met Leu Gly Val Ser Leu
                565                 570                 575

Ala
```

-continued (2) INFORMATION FOR SEQ ID NO: 30:

(i) SEQUENCE CHARACTERISTICS:
        (A) LENGTH: 798 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 30:

```
Met Asn Leu Gln Pro Ile Phe Trp Ile Gly Leu Ile Ser Ser Val Cys
 1               5                  10                  15

Cys Val Phe Ala Gln Thr Asp Glu Asn Arg Cys Leu Lys Ala Asn Ala
                20                  25                  30

Lys Ser Cys Gly Glu Cys Ile Gln Ala Gly Pro Asn Cys Gly Trp Cys
            35                  40                  45

Thr Asn Ser Thr Phe Phe Gln Glu Gly Met Pro Thr Ser Ala Arg Cys
    50                  55                  60

Asp Asp Leu Glu Ala Leu Lys Lys Lys Gly Cys Pro Pro Asp Asp Ile
65                  70                  75                  80

Glu Asn Pro Arg Gly Ser Lys Asp Ile Lys Asn Lys Asn Val Thr
                85                  90                  95

Asn Arg Ser Lys Gly Thr Ala Glu Lys Leu Lys Pro Glu Asp Ile His
                100                 105                 110

Gln Ile Gln Pro Gln Gln Leu Val Leu Arg Leu Arg Ser Gly Glu Pro
            115                 120                 125

Gln Thr Phe Thr Leu Lys Phe Lys Arg Ala Glu Asp Tyr Pro Ile Asp
    130                 135                 140

Leu Tyr Tyr Leu Met Asp Leu Ser Tyr Ser Met Lys Asp Asp Leu Glu
145                 150                 155                 160

Asn Val Lys Ser Leu Gly Thr Asp Leu Met Asn Glu Met Arg Arg Ile
                165                 170                 175

Thr Ser Asp Phe Arg Ile Gly Phe Gly Ser Phe Val Glu Lys Thr Val
                180                 185                 190

Met Pro Tyr Ile Ser Thr Thr Pro Ala Lys Leu Arg Asn Pro Cys Thr
            195                 200                 205

Ser Glu Gln Asn Cys Thr Thr Pro Phe Ser Tyr Lys Asn Val Leu Ser
    210                 215                 220

Leu Thr Asn Lys Gly Glu Val Phe Asn Glu Leu Val Gly Lys Gln Arg
225                 230                 235                 240

Ile Ser Gly Asn Leu Asp Ser Pro Glu Gly Gly Phe Asp Ala Ile Met
                245                 250                 255

Gln Val Ala Val Cys Gly Ser Leu Ile Gly Trp Arg Asn Val Thr Arg
                260                 265                 270

Leu Leu Val Phe Ser Thr Asp Ala Gly Phe His Phe Ala Gly Asp Gly
            275                 280                 285

Lys Leu Gly Gly Ile Val Leu Pro Asn Asp Gly Gln Cys His Leu Glu
    290                 295                 300

Asn Asn Met Tyr Thr Met Ser His Tyr Tyr Asp Tyr Pro Ser Ile Ala
305                 310                 315                 320

His Leu Val Gln Lys Leu Ser Glu Asn Asn Ile Gln Thr Ile Phe Ala
                325                 330                 335

Val Thr Glu Glu Phe Gln Pro Val Tyr Lys Glu Leu Lys Asn Leu Ile
                340                 345                 350
```

```
Pro Lys Ser Ala Val Gly Thr Leu Ser Ala Asn Ser Ser Asn Val Ile
        355                 360                 365

Gln Leu Ile Ile Asp Ala Tyr Asn Ser Leu Ser Ser Glu Val Ile Leu
        370                 375                 380

Glu Asn Gly Lys Leu Ser Glu Gly Val Thr Ile Ser Tyr Lys Ser Tyr
385                 390                 395                 400

Cys Lys Asn Gly Val Asn Gly Thr Gly Glu Asn Gly Arg Lys Cys Ser
                405                 410                 415

Asn Ile Ser Ile Gly Asp Glu Val Gln Phe Glu Ile Ser Ile Thr Ser
                420                 425                 430

Asn Lys Cys Pro Lys Lys Asp Ser Asp Ser Phe Lys Ile Arg Pro Leu
        435                 440                 445

Gly Phe Thr Glu Glu Val Glu Val Ile Leu Gln Tyr Ile Cys Glu Cys
        450                 455                 460

Glu Cys Gln Ser Glu Gly Ile Pro Glu Ser Pro Lys Cys His Glu Gly
465                 470                 475                 480

Asn Gly Thr Phe Glu Cys Gly Ala Cys Arg Cys Asn Glu Gly Arg Val
                485                 490                 495

Gly Arg His Cys Glu Cys Ser Thr Asp Glu Val Asn Ser Glu Asp Met
                500                 505                 510

Asp Ala Tyr Cys Arg Lys Glu Asn Ser Ser Glu Ile Cys Ser Asn Asn
        515                 520                 525

Gly Glu Cys Val Cys Gly Gln Cys Val Cys Arg Lys Arg Asp Asn Thr
        530                 535                 540

Asn Glu Ile Tyr Ser Gly Lys Phe Cys Glu Cys Asp Asn Phe Asn Cys
545                 550                 555                 560

Asp Arg Ser Asn Gly Leu Ile Cys Gly Gly Asn Gly Val Cys Lys Cys
                565                 570                 575

Arg Val Cys Glu Cys Asn Pro Asn Tyr Thr Gly Ser Ala Cys Asp Cys
                580                 585                 590

Ser Leu Asp Thr Ser Thr Cys Glu Ala Ser Asn Gly Gln Ile Cys Asn
        595                 600                 605

Gly Arg Gly Ile Cys Glu Cys Gly Val Cys Lys Cys Thr Asp Pro Lys
        610                 615                 620

Phe Gln Gly Gln Thr Cys Glu Met Cys Gln Thr Cys Leu Gly Val Cys
625                 630                 635                 640

Ala Glu His Lys Glu Cys Val Gln Cys Arg Ala Phe Asn Lys Gly Glu
                645                 650                 655

Lys Lys Asp Thr Cys Thr Gln Glu Cys Ser Tyr Phe Asn Ile Thr Lys
                660                 665                 670

Val Glu Ser Arg Asp Lys Leu Pro Gln Pro Val Gln Pro Asp Pro Val
        675                 680                 685

Ser His Cys Lys Glu Lys Asp Val Asp Asp Cys Trp Phe Tyr Phe Thr
        690                 695                 700

Tyr Ser Val Asn Gly Asn Asn Glu Val Met Val His Val Val Glu Asn
705                 710                 715                 720

Pro Glu Cys Pro Thr Gly Pro Asp Ile Ile Pro Ile Val Ala Gly Val
                725                 730                 735

Val Ala Gly Ile Val Leu Ile Gly Leu Ala Leu Leu Leu Ile Trp Lys
                740                 745                 750

Leu Leu Met Ile Ile His Asp Arg Arg Glu Phe Ala Lys Phe Glu Lys
        755                 760                 765
```

```
Glu Lys Met Asn Ala Lys Trp Asp Thr Gly Glu Asn Pro Ile Tyr Lys
    770                 775                 780

Ser Ala Val Thr Thr Val Val Asn Pro Lys Tyr Glu Gly Lys
785                 790                 795
```

(2) INFORMATION FOR SEQ ID NO: 31:

(i) SEQUENCE CHARACTERISTICS:
        (A) LENGTH: 769 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 31:

```
Met Leu Gly Leu Arg Pro Pro Leu Leu Ala Leu Val Gly Leu Leu Ser
1               5                   10                  15

Leu Gly Cys Val Leu Ser Gln Glu Cys Thr Lys Phe Lys Val Ser Ser
                20                  25                  30

Cys Arg Glu Cys Ile Glu Ser Gly Pro Gly Cys Thr Trp Cys Gln Lys
            35                  40                  45

Leu Asn Phe Thr Gly Pro Gly Asp Pro Asp Ser Ile Arg Cys Asp Thr
        50                  55                  60

Arg Pro Gln Leu Leu Met Arg Gly Cys Ala Ala Asp Asp Ile Met Asp
65                  70                  75                  80

Pro Thr Ser Leu Ala Glu Thr Gln Glu Asp His Asn Gly Gly Gln Lys
                85                  90                  95

Gln Leu Ser Pro Gln Lys Val Thr Leu Tyr Leu Arg Pro Gly Gln Ala
                100                 105                 110

Ala Ala Phe Asn Val Thr Phe Arg Arg Ala Lys Gly Tyr Pro Ile Asp
            115                 120                 125

Leu Tyr Tyr Leu Met Asp Leu Ser Tyr Ser Met Leu Asp Asp Leu Arg
        130                 135                 140

Asn Val Lys Lys Leu Gly Gly Asp Leu Leu Arg Ala Leu Asn Glu Ile
145                 150                 155                 160

Thr Glu Ser Gly Arg Ile Gly Phe Gly Ser Phe Val Asp Lys Thr Val
                165                 170                 175

Leu Pro Phe Val Asn Thr His Pro Asp Lys Leu Arg Asn Pro Cys Pro
            180                 185                 190

Asn Lys Glu Lys Glu Cys Gln Pro Pro Phe Ala Phe Arg His Val Leu
        195                 200                 205

Lys Leu Thr Asn Asn Ser Asn Gln Phe Gln Thr Glu Val Gly Lys Gln
210                 215                 220

Leu Ile Ser Gly Asn Leu Asp Ala Pro Glu Gly Gly Leu Asp Ala Met
225                 230                 235                 240

Met Gln Val Ala Ala Cys Pro Glu Glu Ile Gly Trp Arg Asn Val Thr
                245                 250                 255

Arg Leu Leu Val Phe Ala Thr Asp Asp Gly Phe His Phe Ala Gly Asp
            260                 265                 270

Gly Lys Leu Gly Ala Ile Leu Thr Pro Asn Asp Gly Arg Cys His Leu
        275                 280                 285

Glu Asp Asn Leu Tyr Lys Arg Ser Asn Glu Phe Asp Tyr Pro Ser Val
            290                 295                 300

Gly Gln Leu Ala His Lys Leu Ala Glu Asn Asn Ile Gln Pro Ile Phe
305                 310                 315                 320
```

```
Ala Val Thr Ser Arg Met Val Lys Thr Tyr Glu Lys Leu Thr Glu Ile
                325                 330                 335

Ile Pro Lys Ser Ala Val Gly Glu Leu Ser Glu Asp Ser Ser Asn Val
                340                 345                 350

Val His Leu Ile Lys Asn Ala Tyr Asn Lys Leu Ser Ser Arg Val Phe
                355                 360                 365

Leu Asp His Asn Ala Leu Pro Asp Thr Leu Lys Val Thr Tyr Asp Ser
370                 375                 380

Phe Cys Ser Asn Gly Val Thr His Arg Asn Gln Pro Arg Gly Asp Cys
385                 390                 395                 400

Asp Gly Val Gln Ile Asn Val Pro Ile Thr Phe Gln Val Lys Val Thr
                405                 410                 415

Ala Thr Glu Cys Ile Gln Glu Gln Ser Phe Val Ile Arg Ala Leu Gly
                420                 425                 430

Phe Thr Asp Ile Val Thr Val Gln Val Leu Pro Gln Cys Glu Cys Arg
                435                 440                 445

Cys Arg Asp Gln Ser Arg Asp Arg Ser Leu Cys His Gly Lys Gly Phe
                450                 455                 460

Leu Glu Cys Gly Ile Cys Arg Cys Asp Thr Gly Tyr Ile Gly Lys Asn
465                 470                 475                 480

Cys Glu Cys Gln Thr Gln Gly Arg Ser Ser Gln Glu Leu Glu Gly Ser
                485                 490                 495

Cys Arg Lys Asp Asn Asn Ser Ile Ile Cys Ser Gly Leu Gly Asp Cys
                500                 505                 510

Val Cys Gly Gln Cys Leu Cys His Thr Ser Asp Val Pro Gly Lys Leu
                515                 520                 525

Ile Tyr Gly Gln Tyr Cys Glu Cys Asp Thr Ile Asn Cys Glu Arg Tyr
                530                 535                 540

Asn Gly Gln Val Cys Gly Gly Pro Gly Arg Gly Leu Cys Phe Cys Gly
545                 550                 555                 560

Lys Cys Arg Cys His Pro Gly Phe Glu Gly Ser Ala Cys Gln Cys Glu
                565                 570                 575

Arg Thr Thr Glu Gly Cys Leu Asn Pro Arg Arg Val Glu Cys Ser Gly
                580                 585                 590

Arg Gly Arg Cys Arg Cys Asn Val Cys Glu Cys His Ser Gly Tyr Gln
                595                 600                 605

Leu Pro Leu Cys Gln Glu Cys Pro Gly Cys Pro Ser Pro Cys Gly Lys
                610                 615                 620

Tyr Ile Ser Cys Ala Glu Cys Leu Lys Phe Glu Lys Gly Pro Phe Gly
625                 630                 635                 640

Lys Asn Cys Ser Ala Ala Cys Pro Gly Leu Gln Leu Ser Asn Asn Pro
                645                 650                 655

Val Lys Gly Arg Thr Cys Lys Glu Arg Asp Ser Glu Gly Cys Trp Val
                660                 665                 670

Ala Tyr Thr Leu Glu Gln Gln Asp Gly Met Asp Arg Tyr Leu Ile Tyr
                675                 680                 685

Val Asp Glu Ser Arg Glu Cys Val Ala Gly Pro Asn Ile Ala Ala Ile
                690                 695                 700

Val Gly Gly Thr Val Ala Gly Ile Val Leu Ile Gly Ile Leu Leu Leu
705                 710                 715                 720

Val Ile Trp Lys Ala Leu Ile His Leu Ser Asp Leu Arg Glu Tyr Arg
                725                 730                 735
```

-continued

```
Arg Phe Glu Lys Glu Lys Leu Lys Ser Gln Trp Asn Asn Asp Asn Pro
            740                 745                 750

Leu Phe Lys Ser Ala Thr Thr Thr Val Met Asn Pro Lys Phe Ala Glu
            755                 760                 765

Ser
```

(2) INFORMATION FOR SEQ ID NO: 32:

(i) SEQUENCE CHARACTERISTICS:
        (A) LENGTH: 788 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 32:

```
Met Arg Ala Arg Pro Arg Pro Arg Pro Leu Trp Val Thr Val Leu Ala
1               5                   10                  15

Leu Gly Ala Leu Ala Gly Val Gly Val Gly Gly Pro Asn Ile Cys Thr
            20                  25                  30

Thr Arg Gly Val Ser Ser Cys Gln Gln Cys Leu Ala Val Ser Pro Met
            35                  40                  45

Cys Ala Trp Cys Ser Asp Glu Ala Leu Pro Leu Gly Ser Pro Arg Cys
50                  55                  60

Asp Leu Lys Glu Asn Leu Leu Lys Asp Asn Cys Ala Pro Glu Ser Ile
65                  70                  75                  80

Glu Phe Pro Val Ser Glu Ala Arg Val Leu Glu Asp Arg Pro Leu Ser
            85                  90                  95

Asp Lys Gly Ser Gly Asp Ser Ser Gln Val Thr Gln Val Ser Pro Gln
            100                 105                 110

Arg Ile Ala Leu Arg Leu Arg Pro Asp Asp Ser Lys Asn Phe Ser Ile
            115                 120                 125

Gln Val Arg Gln Val Glu Asp Tyr Pro Val Asp Ile Tyr Tyr Leu Met
            130                 135                 140

Asp Leu Ser Tyr Ser Met Lys Asp Asp Leu Trp Ser Ile Gln Asn Leu
145                 150                 155                 160

Gly Thr Lys Leu Ala Thr Gln Met Arg Lys Leu Thr Ser Asn Leu Arg
            165                 170                 175

Ile Gly Phe Gly Ala Phe Val Asp Lys Pro Val Ser Pro Tyr Met Tyr
            180                 185                 190

Ile Ser Pro Pro Glu Ala Leu Glu Asn Pro Cys Tyr Asp Met Lys Thr
            195                 200                 205

Thr Cys Leu Pro Met Phe Gly Tyr Lys His Val Leu Thr Leu Thr Asp
            210                 215                 220

Gln Val Thr Arg Phe Asn Glu Glu Val Lys Lys Gln Ser Val Ser Arg
225                 230                 235                 240

Asn Arg Asp Ala Pro Glu Gly Gly Phe Asp Ala Ile Met Gln Ala Thr
            245                 250                 255

Val Cys Asp Glu Lys Ile Gly Trp Arg Asn Asp Ala Ser His Leu Leu
            260                 265                 270

Val Phe Thr Thr Asp Ala Lys Thr His Ile Ala Leu Asp Gly Arg Leu
            275                 280                 285

Ala Gly Ile Val Gln Pro Asn Asp Gly Gln Cys His Val Gly Ser Asp
            290                 295                 300
```

```
Asn His Tyr Ser Ala Ser Thr Thr Met Asp Tyr Pro Ser Leu Gly Leu
305                 310                 315                 320

Met Thr Glu Lys Leu Ser Gln Lys Asn Ile Asn Leu Ile Phe Ala Val
            325                 330                 335

Thr Glu Asn Val Val Asn Leu Tyr Gln Asn Tyr Ser Glu Leu Ile Pro
                340                 345                 350

Gly Thr Thr Val Gly Val Leu Ser Met Asp Ser Ser Asn Val Leu Gln
        355                 360                 365

Leu Ile Val Asp Ala Tyr Gly Lys Ile Arg Ser Lys Val Glu Leu Glu
    370                 375                 380

Val Arg Asp Leu Pro Glu Glu Leu Ser Leu Ser Phe Asn Ala Thr Cys
385                 390                 395                 400

Leu Asn Asn Glu Val Ile Pro Gly Leu Lys Ser Cys Met Gly Leu Lys
                405                 410                 415

Ile Gly Asp Thr Val Ser Phe Ser Ile Glu Ala Lys Val Arg Gly Cys
                420                 425                 430

Pro Gln Glu Lys Glu Lys Ser Phe Thr Ile Lys Pro Val Gly Phe Lys
            435                 440                 445

Asp Ser Leu Ile Val Gln Val Thr Phe Asp Cys Asp Cys Ala Cys Gln
    450                 455                 460

Ala Gln Ala Glu Pro Asn Ser His Arg Cys Asn Asn Gly Asn Gly Thr
465                 470                 475                 480

Phe Glu Cys Gly Val Cys Arg Cys Gly Pro Gly Trp Leu Gly Ser Gln
                485                 490                 495

Cys Glu Cys Ser Glu Glu Asp Tyr Arg Pro Ser Gln Gln Asp Glu Cys
                500                 505                 510

Ser Pro Arg Glu Gly Gln Pro Val Cys Ser Gln Arg Gly Glu Cys Leu
    515                 520                 525

Cys Gly Gln Cys Val Cys His Ser Ser Asp Phe Gly Lys Ile Thr Gly
    530                 535                 540

Lys Tyr Cys Glu Cys Asp Asp Phe Ser Cys Val Arg Tyr Lys Gly Glu
545                 550                 555                 560

Met Cys Ser Gly His Gly Gln Cys Ser Cys Gly Asp Cys Leu Cys Asp
                565                 570                 575

Ser Asp Trp Thr Gly Tyr Tyr Cys Asn Cys Thr Thr Arg Thr Asp Thr
                580                 585                 590

Cys Met Ser Ser Asn Gly Leu Leu Cys Ser Gly Arg Gly Lys Cys Glu
        595                 600                 605

Cys Gly Ser Cys Val Cys Ile Gln Pro Gly Ser Tyr Gly Asp Thr Cys
    610                 615                 620

Glu Lys Cys Pro Thr Cys Pro Asp Ala Cys Thr Phe Lys Lys Glu Cys
625                 630                 635                 640

Val Glu Cys Lys Lys Phe Asp Arg Glu Pro Tyr Met Thr Glu Asn Thr
            645                 650                 655

Cys Asn Arg Tyr Cys Arg Asp Glu Ile Glu Ser Val Lys Glu Leu Lys
                660                 665                 670

Asp Thr Gly Lys Asp Ala Val Asn Cys Thr Tyr Lys Asn Glu Asp Asp
            675                 680                 685

Cys Val Val Arg Phe Gln Tyr Tyr Glu Asp Ser Ser Gly Lys Ser Ile
    690                 695                 700

Leu Tyr Val Val Glu Glu Pro Glu Cys Pro Lys Gly Pro Asp Ile Leu
705                 710                 715                 720
```

-continued

```
Val Val Leu Leu Ser Val Met Gly Ala Ile Leu Leu Ile Gly Leu Ala
                725                 730                 735

Ala Leu Leu Ile Trp Lys Leu Leu Ile Thr Ile His Asp Arg Lys Glu
            740                 745                 750

Phe Ala Lys Phe Glu Glu Arg Ala Arg Ala Lys Trp Asp Thr Ala
            755                 760                 765

Asn Asn Pro Leu Tyr Lys Glu Ala Thr Ser Thr Phe Thr Asn Ile Thr
        770                 775                 780

Tyr Arg Gly Thr
785
```

(2) INFORMATION FOR SEQ ID NO: 33:

(i) SEQUENCE CHARACTERISTICS:
      (A) LENGTH: 846 amino acids
      (B) TYPE: amino acid
      (C) STRANDEDNESS: <Unknown>
      (D) TOPOLOGY: linear (ii) MOLECULE TYPE: protein (xi) SEQUENCE DESCRIPTION: SEQ ID NO: 33:

```
Met Ile Leu Glu Arg Asn Arg Arg Cys Gln Leu Ala Leu Leu Met Ile
1               5                  10                  15

Ala Met Leu Ala Ala Ile Ala Ala Gln Thr Asn Ala Gln Lys Ala Ala
            20                  25                  30

Lys Leu Thr Ala Val Ser Thr Cys Ala Ser Lys Glu Lys Cys His Thr
        35                  40                  45

Cys Ile Gln Thr Glu Gly Cys Ala Trp Cys Met Gln Pro Asp Phe Lys
    50                  55                  60

Gly Gln Ser Arg Cys Tyr Gln Asn Thr Ser Ser Leu Cys Pro Glu Glu
65                  70                  75                  80

Phe Ala Tyr Ser Pro Ile Thr Val Glu Gln Ile Leu Val Asn Asn Lys
                85                  90                  95

Leu Thr Asn Gln Tyr Lys Ala Glu Leu Ala Ala Gly Gly Gly Gly Gly
            100                 105                 110

Ala Met Ser Gly Ser Ser Ser Ser Tyr Ser Ser Ser Ser Ser Ser Ser
        115                 120                 125

Ser Ser Phe Tyr Ser Gln Ser Ser Gly Ser Ser Ala Ser Gly
    130                 135                 140

Tyr Glu Glu Tyr Ser Ala Gly Glu Ile Val Gln Ile Gln Pro Gln Ser
145                 150                 155                 160

Met Arg Leu Ala Leu Arg Val Asn Glu Lys His Asn Ile Lys Ile Ser
                165                 170                 175

Tyr Ser Gln Ala Glu Gly Tyr Pro Val Asp Leu Tyr Tyr Leu Met Asp
            180                 185                 190

Leu Ser Lys Ser Met Glu Asp Asp Lys Ala Lys Leu Ser Thr Leu Gly
        195                 200                 205

Asp Lys Leu Ser Glu Thr Met Lys Arg Ile Thr Asn Asn Phe His Leu
    210                 215                 220

Gly Phe Gly Ser Phe Val Asp Lys Val Leu Met Pro Tyr Val Ser Thr
225                 230                 235                 240

Ile Pro Lys Lys Leu Glu His Pro Cys Glu Asn Cys Lys Ala Pro Tyr
                245                 250                 255

Gly Tyr Gln Asn His Met Pro Leu Asn Asn Asn Thr Glu Ser Phe Ser
            260                 265                 270
```

```
Asn Glu Val Lys Asn Ala Thr Val Ser Gly Asn Leu Asp Ala Pro Glu
            275                 280                 285

Gly Gly Phe Asp Ala Ile Met Gln Ala Ile Ala Cys Arg Ser Gln Ile
        290                 295                 300

Gly Trp Arg Glu Gln Ala Arg Arg Leu Leu Val Phe Ser Thr Asp Ala
305                 310                 315                 320

Gly Phe His Tyr Ala Gly Asp Gly Lys Leu Gly Gly Val Ile Ala Pro
                325                 330                 335

Asn Asp Gly Glu Cys His Leu Ser Pro Lys Gly Glu Tyr Thr His Ser
            340                 345                 350

Thr Leu Gln Asp Tyr Pro Ser Ile Ser Gln Ile Asn Gln Lys Val Lys
            355                 360                 365

Asp Asn Ala Ile Asn Ile Phe Ala Val Thr Ala Ser Gln Leu Ser
370                 375                 380

Val Tyr Glu Lys Leu Val Glu His Ile Gln Gly Ser Ser Ala Ala Lys
385                 390                 395                 400

Leu Asp Asn Asp Ser Ser Asn Val Val Glu Leu Val Lys Glu Glu Tyr
                405                 410                 415

Arg Lys Ile Ser Ser Val Glu Met Lys Asp Asn Ala Thr Gly Asp
            420                 425                 430

Val Lys Ile Thr Tyr Phe Ser Ser Cys Leu Ser Asn Gly Pro Glu Val
            435                 440                 445

Gln Thr Ser Lys Cys Asp Asn Leu Lys Glu Gly Gln Gln Val Ser Phe
        450                 455                 460

Thr Ala Gln Ile Gln Leu Leu Lys Cys Pro Glu Asp Pro Arg Asp Trp
465                 470                 475                 480

Thr Gln Thr Ile His Ile Ser Pro Val Gly Ile Asn Glu Val Met Gln
                485                 490                 495

Ile Gln Leu Thr Met Leu Cys Ser Cys Pro Cys Glu Asn Pro Gly Ser
            500                 505                 510

Ile Gly Tyr Gln Val Gln Ala Asn Ser Cys Ser Gly His Gly Thr Ser
            515                 520                 525

Met Cys Gly Ile Cys Asn Cys Asp Asp Ser Tyr Phe Gly Asn Lys Cys
        530                 535                 540

Glu Cys Ser Ala Thr Asp Leu Thr Ser Lys Phe Ala Asn Asp Thr Ser
545                 550                 555                 560

Cys Arg Ala Asp Ser Thr Ser Thr Asp Cys Ser Gly Arg Gly His
                565                 570                 575

Cys Cys Val Gly Ala Cys Glu Cys His Lys Arg Pro Asn Pro Ile Glu
            580                 585                 590

Ile Ile Ser Gly Lys His Cys Glu Cys Asp Asn Phe Ser Cys Glu Arg
            595                 600                 605

Asn Arg Asn Gln Leu Cys Ser Gly Pro Asp His Gly Thr Cys Glu Cys
        610                 615                 620

Gly Arg Cys Lys Cys Lys Pro Gly Trp Thr Gly Ser Asn Cys Gly Cys
625                 630                 635                 640

Gln Glu Ser Asn Asp Thr Cys Met Pro Gly Gly Gly Glu Ile Cys
                645                 650                 655

Ser Gly His Gly Thr Cys Glu Cys Gly Val Cys Lys Cys Thr Val Asn
            660                 665                 670

Asp Gln Gly Arg Phe Ser Gly Arg His Cys Glu Lys Cys Pro Thr Cys
            675                 680                 685
```

```
Ser Gly Arg Cys Gln Glu Leu Lys Asp Cys Val Gln Cys Gln Met Tyr
    690                 695                 700
Lys Thr Gly Glu Leu Lys Asn Gly Asp Asp Cys Ala Arg Asn Cys Thr
705                 710                 715                 720
Gln Phe Val Pro Val Gly Val Glu Lys Val Glu Ile Asp Glu Thr Lys
                725                 730                 735
Asp Glu Gln Met Cys Lys Phe Phe Asp Glu Asp Cys Lys Phe Met
            740                 745                 750
Phe Lys Tyr Ser Glu Gln Gly Glu Leu His Val Tyr Ala Gln Glu Asn
        755                 760                 765
Lys Glu Cys Pro Ala Lys Val Phe Met Leu Gly Ile Val Met Gly Val
    770                 775                 780
Ile Ala Ala Ile Val Leu Val Gly Leu Ala Ile Leu Leu Leu Trp Lys
785                 790                 795                 800
Leu Leu Thr Thr Ile His Asp Arg Arg Glu Phe Ala Arg Phe Glu Lys
                805                 810                 815
Glu Arg Met Asn Ala Lys Trp Asp Thr Gly Glu Asn Pro Ile Tyr Lys
            820                 825                 830
Gln Ala Thr Ser Thr Phe Lys Asn Pro Met Tyr Ala Gly Lys
        835                 840                 845

(2) INFORMATION FOR SEQ ID NO: 34:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..282

(xi) SEQUENCE DESCRIPTION: SEQ ID NO: 34:

TGT GTT TGT AGG AAG AGG GAT AAT ACA AAT GAA ATT TAT TCT GGC AAA      48
Cys Val Cys Arg Lys Arg Asp Asn Thr Asn Glu Ile Tyr Ser Gly Lys
  1               5                   10                  15

TTC TGC GAG TGT GAT AAT TTC AAC TGT GAT AGA TCC AAT GGC TTA ATT      96
Phe Cys Glu Cys Asp Asn Phe Asn Cys Asp Arg Ser Asn Gly Leu Ile
                20                  25                  30

TGT GGA GGA AAT GGT GTT TGC AAG TGT CGT GTG TGT GAG TGC AAC CCC     144
Cys Gly Gly Asn Gly Val Cys Lys Cys Arg Val Cys Glu Cys Asn Pro
            35                  40                  45

AAC TAC ACT GGC AGT GCA TGT GAC TGT TCT TTG GAT ACT AGT ACT TGT     192
Asn Tyr Thr Gly Ser Ala Cys Asp Cys Ser Leu Asp Thr Ser Thr Cys
        50                  55                  60

GAA GCC AGC AAC GGA CAG ATC TGC AAT GGC CGG GGC ATC TGC GAG TGT     240
Glu Ala Ser Asn Gly Gln Ile Cys Asn Gly Arg Gly Ile Cys Glu Cys
65                  70                  75                  80

GGT GTC TGT AAG TGT ACA GAT CCG AAG TTT CAA GGG CAA ACG             282
Gly Val Cys Lys Cys Thr Asp Pro Lys Phe Gln Gly Gln Thr
                85                  90

(2) INFORMATION FOR SEQ ID NO: 35:

(i) SEQUENCE CHARACTERISTICS:
        (A) LENGTH: 94 amino acids
        (B) TYPE: amino acid
        (D) TOPOLOGY: linear
```

(ii) MOLECULE TYPE: protein (xi) SEQUENCE DESCRIPTION: SEQ ID NO: 35:

| Cys | Val | Cys | Arg | Lys | Arg | Asp | Asn | Thr | Asn | Glu | Ile | Tyr | Ser | Gly | Lys |
|-----|-----|-----|-----|-----|-----|-----|-----|-----|-----|-----|-----|-----|-----|-----|-----|
| 1 | | | | 5 | | | | | 10 | | | | | 15 | |

| Phe | Cys | Glu | Cys | Asp | Asn | Phe | Asn | Cys | Asp | Arg | Ser | Asn | Gly | Leu | Ile |
|-----|-----|-----|-----|-----|-----|-----|-----|-----|-----|-----|-----|-----|-----|-----|-----|
| | | | 20 | | | | | 25 | | | | | 30 | | |

| Cys | Gly | Gly | Asn | Gly | Val | Cys | Lys | Cys | Arg | Val | Cys | Glu | Cys | Asn | Pro |
|-----|-----|-----|-----|-----|-----|-----|-----|-----|-----|-----|-----|-----|-----|-----|-----|
| | | 35 | | | | | 40 | | | | | 45 | | | |

| Asn | Tyr | Thr | Gly | Ser | Ala | Cys | Asp | Cys | Ser | Leu | Asp | Thr | Ser | Thr | Cys |
|-----|-----|-----|-----|-----|-----|-----|-----|-----|-----|-----|-----|-----|-----|-----|-----|
| | 50 | | | | | 55 | | | | | 60 | | | | |

| Glu | Ala | Ser | Asn | Gly | Gln | Ile | Cys | Asn | Gly | Arg | Gly | Ile | Cys | Glu | Cys |
|-----|-----|-----|-----|-----|-----|-----|-----|-----|-----|-----|-----|-----|-----|-----|-----|
| 65 | | | | | 70 | | | | | 75 | | | | | 80 |

| Gly | Val | Cys | Lys | Cys | Thr | Asp | Pro | Lys | Phe | Gln | Gly | Gln | Thr |
|-----|-----|-----|-----|-----|-----|-----|-----|-----|-----|-----|-----|-----|-----|
| | | | | 85 | | | | | 90 | | | | |

(2) INFORMATION FOR SEQ ID NO: 36:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..282

(xi) SEQUENCE DESCRIPTION: SEQ ID NO: 36:

| TGC | GTG | TGC | AGG | AAG | AGG | GAC | AAC | ACC | AAC | GAG | ATC | TAC | TCG | GGC | AAA | 48 |
| Cys | Val | Cys | Arg | Lys | Arg | Asp | Asn | Thr | Asn | Glu | Ile | Tyr | Ser | Gly | Lys | |
| 1 | | | | 5 | | | | | 10 | | | | | 15 | | |

| TTC | TGC | GAG | TGC | GAC | AAC | TTC | AAC | TGT | GAT | CGG | TCC | AAT | GGC | TTA | ATC | 96 |
| Phe | Cys | Glu | Cys | Asp | Asn | Phe | Asn | Cys | Asp | Arg | Ser | Asn | Gly | Leu | Ile | |
| | | | 20 | | | | | 25 | | | | | 30 | | | |

| TGT | GGA | GGC | AAT | GGA | GTG | TGC | CGG | TGT | CGT | GTG | TGC | GAG | TGC | TTC | CCC | 144 |
| Cys | Gly | Gly | Asn | Gly | Val | Cys | Arg | Cys | Arg | Val | Cys | Glu | Cys | Phe | Pro | |
| | | 35 | | | | | 40 | | | | | 45 | | | | |

| AAC | TAC | ACC | GGC | AGC | GCC | TGT | GAC | TGC | TCT | CTG | GAC | ACT | GCG | CCG | TGC | 192 |
| Asn | Tyr | Thr | Gly | Ser | Ala | Cys | Asp | Cys | Ser | Leu | Asp | Thr | Ala | Pro | Cys | |
| | 50 | | | | | 55 | | | | | 60 | | | | | |

| CTG | GCC | ACC | AAC | GGG | CAG | ATC | TGC | AAT | GGC | CGG | GGT | GTG | TGC | GAG | TGC | 240 |
| Leu | Ala | Thr | Asn | Gly | Gln | Ile | Cys | Asn | Gly | Arg | Gly | Val | Cys | Glu | Cys | |
| 65 | | | | | 70 | | | | | 75 | | | | | 80 | |

| GGC | GTG | TGC | AAG | TGC | ACG | GAC | CCC | AAG | TTC | CAG | GGG | CAG | ACC | | | 282 |
| Gly | Val | Cys | Lys | Cys | Thr | Asp | Pro | Lys | Phe | Gln | Gly | Gln | Thr | | | |
| | | | | 85 | | | | | 90 | | | | | | | |

(2) INFORMATION FOR SEQ ID NO: 37:

(i) SEQUENCE CHARACTERISTICS:
        (A) LENGTH: 94 amino acids
        (B) TYPE: amino acid
        (D) TOPOLOGY: linear (ii) MOLECULE TYPE: protein (xi) SEQUENCE DESCRIPTION: SEQ ID NO: 37:

| Cys | Val | Cys | Arg | Lys | Arg | Asp | Asn | Thr | Asn | Glu | Ile | Tyr | Ser | Gly | Lys |
|-----|-----|-----|-----|-----|-----|-----|-----|-----|-----|-----|-----|-----|-----|-----|-----|
| 1 | | | | 5 | | | | | 10 | | | | | 15 | |

```
Phe Cys Glu Cys Asp Asn Phe Asn Cys Asp Arg Ser Asn Gly Leu Ile
                20                  25                  30

Cys Gly Gly Asn Gly Val Cys Arg Cys Arg Val Cys Glu Cys Phe Pro
            35                  40                  45

Asn Tyr Thr Gly Ser Ala Cys Asp Cys Ser Leu Asp Thr Ala Pro Cys
        50                  55                  60

Leu Ala Thr Asn Gly Gln Ile Cys Asn Gly Arg Gly Val Cys Glu Cys
 65                  70                  75                  80

Gly Val Cys Lys Cys Thr Asp Pro Lys Phe Gln Gly Gln Thr
                85                  90
```

(2) INFORMATION FOR SEQ ID NO: 38:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..276

(xi) SEQUENCE DESCRIPTION: SEQ ID NO: 38:

```
TGT GTC TGC CAC AGC AGT GAC TTT GGC AAG ATC ACG GGC AAG TAC TGC        48
Cys Val Cys His Ser Ser Asp Phe Gly Lys Ile Thr Gly Lys Tyr Cys
 1               5                  10                  15

GAG TGT GAC GAC TTC TCC TGT GTC CGC TAC AAG GGG GAG ATG TGC TCA        96
Glu Cys Asp Asp Phe Ser Cys Val Arg Tyr Lys Gly Glu Met Cys Ser
                20                  25                  30

GGC CAT GGC CAG TGC AGC TGT GGG GAC TGC CTG TGT GAC TCC GAC TGG       144
Gly His Gly Gln Cys Ser Cys Gly Asp Cys Leu Cys Asp Ser Asp Trp
            35                  40                  45

ACC GGC TAC TAC TGC AAC TGT ACC ACG CGT ACT GAC ACC TGC ATG TCC       192
Thr Gly Tyr Tyr Cys Asn Cys Thr Thr Arg Thr Asp Thr Cys Met Ser
        50                  55                  60

AGC AAT GGG CTG CTG TGC AGC GGC CGC GGC AAG TGT GAA TGT GGC AGC       240
Ser Asn Gly Leu Leu Cys Ser Gly Arg Gly Lys Cys Glu Cys Gly Ser
 65                  70                  75                  80

TGT GTC TGT ATC CAG CCG GGC TCC TAT GGG GAC ACC                       276
Cys Val Cys Ile Gln Pro Gly Ser Tyr Gly Asp Thr
                85                  90
```

(2) INFORMATION FOR SEQ ID NO: 39:

(i) SEQUENCE CHARACTERISTICS:
        (A) LENGTH: 92 amino acids
        (B) TYPE: amino acid
        (D) TOPOLOGY: linear (ii) MOLECULE TYPE: protein (xi) SEQUENCE DESCRIPTION: SEQ ID NO: 39:

```
Cys Val Cys His Ser Ser Asp Phe Gly Lys Ile Thr Gly Lys Tyr Cys
 1               5                  10                  15

Glu Cys Asp Asp Phe Ser Cys Val Arg Tyr Lys Gly Glu Met Cys Ser
                20                  25                  30

Gly His Gly Gln Cys Ser Cys Gly Asp Cys Leu Cys Asp Ser Asp Trp
            35                  40                  45

Thr Gly Tyr Tyr Cys Asn Cys Thr Thr Arg Thr Asp Thr Cys Met Ser
        50                  55                  60
```

```
Ser Asn Gly Leu Leu Cys Ser Gly Arg Gly Lys Cys Glu Cys Gly Ser
 65                  70                  75                  80

Cys Val Cys Ile Gln Pro Gly Ser Tyr Gly Asp Thr
                 85                  90
```

(2) INFORMATION FOR SEQ ID NO: 40:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..276

(xi) SEQUENCE DESCRIPTION: SEQ ID NO: 40:

```
TGC TCC TGC CAC AGC GAT GAC TTT GGC AAG ATC ACG GGC AAG TAC TGT      48
Cys Ser Cys His Ser Asp Asp Phe Gly Lys Ile Thr Gly Lys Tyr Cys
 1               5                  10                  15

GAG TGT GAT GAC TTC TCC TGT GTT CGC TAC AAA GGG GAG ATG TGC TCA      96
Glu Cys Asp Asp Phe Ser Cys Val Arg Tyr Lys Gly Glu Met Cys Ser
                 20                  25                  30

GGC CAT GGC CAG TGC AGC TGT GGG GAT TGC CTG TGT GAT TCT GAC TGG     144
Gly His Gly Gln Cys Ser Cys Gly Asp Cys Leu Cys Asp Ser Asp Trp
             35                  40                  45

ACT GGC TAC TAC TGT AAC TGT ACC ACA CTC ACT GAC ACC TGC ATG TCC     192
Thr Gly Tyr Tyr Cys Asn Cys Thr Thr Leu Thr Asp Thr Cys Met Ser
 50                  55                  60

AGC AAC GGG CTG TTG TGC AGC GGC CGG GGC AAG TGT GAA TGT GGC AGT     240
Ser Asn Gly Leu Leu Cys Ser Gly Arg Gly Lys Cys Glu Cys Gly Ser
 65                  70                  75                  80

TGT GTC TGC ATC CAG CCG GGA TCT TAT GGG GAC ACT                     276
Cys Val Cys Ile Gln Pro Gly Ser Tyr Gly Asp Thr
                 85                  90
```

(2) INFORMATION FOR SEQ ID NO: 41:

(i) SEQUENCE CHARACTERISTICS:
        (A) LENGTH: 92 amino acids
        (B) TYPE: amino acid
        (D) TOPOLOGY: linear (ii) MOLECULE TYPE: protein (xi) SEQUENCE DESCRIPTION: SEQ ID NO: 41:

```
Cys Ser Cys His Ser Asp Asp Phe Gly Lys Ile Thr Gly Lys Tyr Cys
 1               5                  10                  15

Glu Cys Asp Asp Phe Ser Cys Val Arg Tyr Lys Gly Glu Met Cys Ser
                 20                  25                  30

Gly His Gly Gln Cys Ser Cys Gly Asp Cys Leu Cys Asp Ser Asp Trp
             35                  40                  45

Thr Gly Tyr Tyr Cys Asn Cys Thr Thr Leu Thr Asp Thr Cys Met Ser
 50                  55                  60

Ser Asn Gly Leu Leu Cys Ser Gly Arg Gly Lys Cys Glu Cys Gly Ser
 65                  70                  75                  80

Cys Val Cys Ile Gln Pro Gly Ser Tyr Gly Asp Thr
                 85                  90
```

(2) INFORMATION FOR SEQ ID NO: 42:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..276

(xi) SEQUENCE DESCRIPTION: SEQ ID NO: 42:

```
TGT ATC TGC CAC TTG TCT CCC TAT GGA AAC ATT TAT GGA CCT TAT TGC      48
Cys Ile Cys His Leu Ser Pro Tyr Gly Asn Ile Tyr Gly Pro Tyr Cys
 1               5                  10                  15

CAG TGT GAC AAT TTC TCC TGC GTG AGA CAC AAA GGG CTG CTC TGC GGA      96
Gln Cys Asp Asn Phe Ser Cys Val Arg His Lys Gly Leu Leu Cys Gly
                20                  25                  30

GGT AAC GGC GAC TGT GAC TGT GGT GAA TGT GTG TGC AGG AGC GGC TGG     144
Gly Asn Gly Asp Cys Asp Cys Gly Glu Cys Val Cys Arg Ser Gly Trp
         35                  40                  45

ACT GGC GAG TAC TGC AAC TGC ACC ACC AGC ACG GAC TCC TGC GTC TCT     192
Thr Gly Glu Tyr Cys Asn Cys Thr Thr Ser Thr Asp Ser Cys Val Ser
 50                  55                  60

GAA GAT GGA GTG CTC TGC AGC GGG CGC GGG GAC TGT GTT TGT GGC AAG     240
Glu Asp Gly Val Leu Cys Ser Gly Arg Gly Asp Cys Val Cys Gly Lys
 65                  70                  75                  80

TGT GTT TGC ACA AAC CCT GGA GCC TCA GGA CCA ACC                     276
Cys Val Cys Thr Asn Pro Gly Ala Ser Gly Pro Thr
                 85                  90
```

(2) INFORMATION FOR SEQ ID NO: 43:

(i) SEQUENCE CHARACTERISTICS:
        (A) LENGTH: 92 amino acids
        (B) TYPE: amino acid
        (D) TOPOLOGY: linear (ii) MOLECULE TYPE: protein (xi) SEQUENCE DESCRIPTION: SEQ ID NO: 43:

```
Cys Ile Cys His Leu Ser Pro Tyr Gly Asn Ile Tyr Gly Pro Tyr Cys
 1               5                  10                  15

Gln Cys Asp Asn Phe Ser Cys Val Arg His Lys Gly Leu Leu Cys Gly
                20                  25                  30

Gly Asn Gly Asp Cys Asp Cys Gly Glu Cys Val Cys Arg Ser Gly Trp
         35                  40                  45

Thr Gly Glu Tyr Cys Asn Cys Thr Thr Ser Thr Asp Ser Cys Val Ser
 50                  55                  60

Glu Asp Gly Val Leu Cys Ser Gly Arg Gly Asp Cys Val Cys Gly Lys
 65                  70                  75                  80

Cys Val Cys Thr Asn Pro Gly Ala Ser Gly Pro Thr
                 85                  90
```

(2) INFORMATION FOR SEQ ID NO: 44:

(i) SEQUENCE CHARACTERISTICS:
        (A) LENGTH: 276 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..276

(xi) SEQUENCE DESCRIPTION: SEQ ID NO: 44:

| TGC | ATC | TGC | CAC | TTG | TCT | CCC | TAT | GGA | AAC | ATT | TAT | GGA | CCT | TAC | TGC | 48 |
|---|---|---|---|---|---|---|---|---|---|---|---|---|---|---|---|---|
| Cys | Ile | Cys | His | Leu | Ser | Pro | Tyr | Gly | Asn | Ile | Tyr | Gly | Pro | Tyr | Cys | |
| 1 | | | | 5 | | | | | 10 | | | | | 15 | | |

| CAG | TGT | GAC | AAT | TTC | TCC | TGT | GTG | AGG | CAC | AAA | GGG | CTG | CTC | TGT | GGA | 96 |
|---|---|---|---|---|---|---|---|---|---|---|---|---|---|---|---|---|
| Gln | Cys | Asp | Asn | Phe | Ser | Cys | Val | Arg | His | Lys | Gly | Leu | Leu | Cys | Gly | |
| | | | 20 | | | | | 25 | | | | | 30 | | | |

| GAT | AAC | GGA | GAC | TGT | GAA | TGT | GGG | GAA | TGC | GTG | TGC | AGG | AGT | GGT | TGG | 144 |
|---|---|---|---|---|---|---|---|---|---|---|---|---|---|---|---|---|
| Asp | Asn | Gly | Asp | Cys | Glu | Cys | Gly | Glu | Cys | Val | Cys | Arg | Ser | Gly | Trp | |
| | | 35 | | | | | 40 | | | | | 45 | | | | |

| ACC | GGA | GAG | TAC | TGC | AAC | TGT | ACC | ACC | AGC | ACA | GAC | ACC | TGC | ATC | TCC | 192 |
|---|---|---|---|---|---|---|---|---|---|---|---|---|---|---|---|---|
| Thr | Gly | Glu | Tyr | Cys | Asn | Cys | Thr | Thr | Ser | Thr | Asp | Thr | Cys | Ile | Ser | |
| | 50 | | | | | 55 | | | | | 60 | | | | | |

| GAA | GAC | GGC | ACG | CTC | TGC | AGC | GGG | CGC | GGG | GAC | TGC | GTC | TGT | GGC | AAG | 240 |
|---|---|---|---|---|---|---|---|---|---|---|---|---|---|---|---|---|
| Glu | Asp | Gly | Thr | Leu | Cys | Ser | Gly | Arg | Gly | Asp | Cys | Val | Cys | Gly | Lys | |
| 65 | | | | 70 | | | | | 75 | | | | | 80 | | |

| TGT | GTC | TGC | ACG | AAC | CCT | GGA | GCC | TCG | GGA | CCC | ACC | | | | | 276 |
|---|---|---|---|---|---|---|---|---|---|---|---|---|---|---|---|---|
| Cys | Val | Cys | Thr | Asn | Pro | Gly | Ala | Ser | Gly | Pro | Thr | | | | | |
| | | | 85 | | | | | 90 | | | | | | | | |

(2) INFORMATION FOR SEQ ID NO: 45:

(i) SEQUENCE CHARACTERISTICS:
        (A) LENGTH: 92 amino acids
        (B) TYPE: amino acid
        (D) TOPOLOGY: linear (ii) MOLECULE TYPE: protein (xi) SEQUENCE DESCRIPTION: SEQ ID NO: 45:

Cys Ile Cys His Leu Ser Pro Tyr Gly Asn Ile Tyr Gly Pro Tyr Cys
1               5                   10                  15

Gln Cys Asp Asn Phe Ser Cys Val Arg His Lys Gly Leu Leu Cys Gly
            20                  25                  30

Asp Asn Gly Asp Cys Glu Cys Gly Glu Cys Val Cys Arg Ser Gly Trp
        35                  40                  45

Thr Gly Glu Tyr Cys Asn Cys Thr Thr Ser Thr Asp Thr Cys Ile Ser
    50                  55                  60

Glu Asp Gly Thr Leu Cys Ser Gly Arg Gly Asp Cys Val Cys Gly Lys
65                  70                  75                  80

Cys Val Cys Thr Asn Pro Gly Ala Ser Gly Pro Thr
            85                  90

(2) INFORMATION FOR SEQ ID NO: 46:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 46:

Ser Xaa Ser Met Xaa Asp Asp Leu
1               5

(2) INFORMATION FOR SEQ ID NO: 47:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 47:

```
Gly Phe Gly Ser Phe Val
1               5
```

(2) INFORMATION FOR SEQ ID NO: 48:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 48:

```
Arg Gly Ser Thr Ser Thr Phe Lys Asn Val Thr Tyr Lys His Arg
1               5                   10                  15
```

(2) INFORMATION FOR SEQ ID NO: 49:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 49:

```
Tyr Lys His Arg Glu Lys Gln Lys Val Asp Leu Ser Thr Asp Cys
1               5                   10                  15
```

(2) INFORMATION FOR SEQ ID NO: 50:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 50:

```
Asp Leu Tyr Tyr Leu Met Asp Leu
1               5
```

(2) INFORMATION FOR SEQ ID NO: 51:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 51:

```
Glu Gly Gly Leu Asp Ala Met Met Gln
1               5
```

```
(2) INFORMATION FOR SEQ ID NO: 52:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 52:

Asp Ile Tyr Tyr Leu Met Asp Leu
1               5

(2) INFORMATION FOR SEQ ID NO: 53:

(i) SEQUENCE CHARACTERISTICS:
        (A) LENGTH: 9 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 53:

Glu Gly Gly Phe Asp Ala Ile Met Gln
1               5

(2) INFORMATION FOR SEQ ID NO: 54:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 54:

Gly Asp Cys Val Cys Gly Gln Cys
1               5

(2) INFORMATION FOR SEQ ID NO: 55:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 55:

Ile Gly Ile Leu Leu Leu Val Ile Trp Lys
1               5                   10

(2) INFORMATION FOR SEQ ID NO: 56:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 56:

Gly Glu Cys Leu Cys Gly Gln Cys
1               5
```

```
(2) INFORMATION FOR SEQ ID NO: 57:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 57:

Ile Gly Leu Ala Ala Leu Leu Ile Trp Lys
1               5                   10

(2) INFORMATION FOR SEQ ID NO: 58:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 58:

Gly Glu Cys Val Cys Gly Gln Cys
1               5

(2) INFORMATION FOR SEQ ID NO: 59:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 59:

Ile Gly Leu Ala Leu Leu Leu Ile Trp Lys
1               5                   10

(2) INFORMATION FOR SEQ ID NO: 60:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 60:

Gly Glu Cys Ile Cys Gly Gln Cys
1               5

(2) INFORMATION FOR SEQ ID NO: 61:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 61:

Pro Leu Thr Asn Asp Ala Glu Arg
1               5
```

-continued

```
(2) INFORMATION FOR SEQ ID NO: 62:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 62:

Ile Ser Glu Asp Gly
1               5
```

We claim:

1. A method of expressing an integrin $\beta_6$ subunit in a cell and selecting a cell with increased adhesion, the method comprising introducing into to cell an expression vector comprising a polynucleotide encoding SEQ ID NO:27, thereby expressing the $\beta_6$ subunit in the cell, and selecting a cell with increased adhesion to fibronectin or vitronectin.

* * * * *

UNITED STATES PATENT AND TRADEMARK OFFICE
CERTIFICATE OF CORRECTION

PATENT NO. : 6,787,322 B2
DATED : September 7, 2004
INVENTOR(S) : Dean Sheppard et al.

It is certified that error appears in the above-identified patent and that said Letters Patent is hereby corrected as shown below:

<u>Column 77,</u>
Line 20, kindly delete "introducing into to cell" and replace it with -- introducing into the cell --

Signed and Sealed this

First Day of February, 2005

JON W. DUDAS
*Director of the United States Patent and Trademark Office*